US006288034B1

(12) United States Patent
Murgita

(10) Patent No.: US 6,288,034 B1
(45) Date of Patent: *Sep. 11, 2001

(54) RECOMBINANT HUMAN ALPHA-FETOPROTEIN AS AN IMMUNOSUPPRESSIVE AGENT

(75) Inventor: Robert A. Murgita, Montreal (CA)

(73) Assignee: Martinex R & D Inc. (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/186,723

(22) Filed: Nov. 5, 1998

Related U.S. Application Data

(63) Continuation of application No. 08/377,309, filed on Jan. 24, 1995, now Pat. No. 5,965,528.

(51) Int. Cl.$^7$ ............................. A61K 38/00; C07K 14/47

(52) U.S. Cl. ............................................. 514/12; 530/350

(58) Field of Search ........................ 514/11, 12; 435/69.1; 424/88

(56) References Cited

U.S. PATENT DOCUMENTS

| | | | |
|---|---|---|---|
| 4,692,332 | 9/1987 | McMichael | 424/88 |
| 4,877,610 | 10/1989 | McMichael | 424/88 |
| 4,966,753 | 10/1990 | McMichael | 424/88 |
| 4,970,071 | 11/1990 | McMichael | 424/88 |
| 4,996,193 | 2/1991 | Hewitt et al. | 514/11 |
| 5,130,415 | 7/1992 | Tecce et al. | 530/324 |
| 5,206,153 | 4/1993 | Tamaoki et al. | 435/69.7 |
| 5,365,948 | 11/1994 | McMichael | 128/898 |
| 5,384,250 | 1/1995 | Murgita | 435/69.1 |

FOREIGN PATENT DOCUMENTS

| | | |
|---|---|---|
| 0 001 812 | 5/1979 | (EP) . |
| 20058666 | 1/1990 | (JP) . |
| WO 86/04241 | 7/1986 | (WO) . |
| WO 93/05774 | 4/1993 | (WO) . |
| WO 94/10199 | 5/1994 | (WO) . |

OTHER PUBLICATIONS

Abramsky et al., "Alpha–fetoprotein Suppresses Experimental Allergic Encephalomyelitis," Journal of Neuroimmunology 2:1–7 (1982).

Abramsky et al., Annals New York Academy of Sciences, pp. 108–115 (1983).

Aoyagi et al., "Differential Reactivity of α–Fetoprotein with Lectins and Evaluation of Its Usefulness in the Diagnosis of Hepatocellular Carcinoma", Gann 75:809–815 (1984).

Biddle et al., "Specific Cytoplasmic Alpha–fetoprotein Binding Protein In MCF–7 Human Breast Cancer Cells and Primary Breast Cancer Tissue," Breast Cancer Research and Treatment 10:279–286 (1987).

Boismenu et al., "Expression of Domains of Mouse Alpha–Fetoprotein in *Escherichia coli*," Life Sciences 43:673–681 (1988).

Brenner et al., "Influence Of Alpha–fetoprotein On The In Vitro And In Vivo Immune Response To Acetylcholine Receptor," Annals New York Academy of Sciences 377:208–221 (1981).

Brenner et al., "Inhibitory Effect Of α–fetoprotein On the Binding Of *Myasthenia gravis*Antibody To Acetylcholine Receptor," Proc. Natl. Acad. Sci. USA 77:3635–3639(1980).

Brenner et al., "Immunosuppression of Experimental Autoimmune *Myasthenia gravis* by Alpha–Fetoprotein Rich Formation," Immunology Letters 3:163–167 (1981).

Buamah et al., "Serum alpha fetoprotein heterogeneity as a means of differentiating between primary hepatocellular carcinoma and hepatic secondaries," Clinica Chimica Acta. 139:313–316 (1984).

Buschman et al., "Experimental *Myasthenia gravis* Induced in Mice by Passive Transfer of Human Myasthenic Immunoglobulin," Journal of Neuroimmunology, 13:315–330 (1987).

Cohen et al., "Suppression by Alpha–Fetoprotein of Murine Natural Killer Cell Activity Stimulated in Vitro and in Vivo by Interferon and Interleukin 2," Scand. J. Immunol. 23:211–223 (1986).

Dattwyler et al., "Binding Of α–foetoprotein To Murine T Cells," Nature 256:656–657 (1975).

Fialova et al., "Serum Levels of Trophoblast–Specific Beta–1–Globulin (SP1) and Alpha–1–Fetoprotein (AFP) in Pregnant Women With Rheumatoid Arthritis," Ceskoslovenska Gynekologie 56:166–170 (1991) (Abstract only).

Gershwin et al., "The Influence of α–Fetoprotein on Moloney Sarcoma Virus Oncogenesis: Evidence For Generation of Antigen Nonspecific Suppressor T Cells," The Journal of Immunology 121:2292–2297 (1978).

Giuliani et al., "Synthesis And Characterization Of A Recombinant Fragment Of Human α–fetoprotein With Antigenic Selectivity Versus Albumin," Protein Engineering 2:605–610 (1989).

Glazier et al., "Graft–Versus–Host Disease in Cyclosporin A–Treated Rats After Syngeneic and Autologous Bone Marrow Reconstitution," J. Exp. Med. 158:1–8 (1983).

Goidl et al., "Studies On The Mechanisms of Alpha–Fetoprotein Induction of Immune Suppressive Activity," Developmental Immunobiology pp. 35–55 (1979).

(List continued on next page.)

*Primary Examiner*—Kenneth R. Horlick
*Assistant Examiner*—Teresa Strzelecka
(74) *Attorney, Agent, or Firm*—Clark & Elbing LLP

(57) ABSTRACT

Disclosed are methods of inhibiting autoreactive immune cell proliferation in a mammal, involving administering to the mammal a therapeutically effective amount of recombinant human alpha-fetoprotein or an immune cell antiproliferative fragment or analog thereof.

13 Claims, 7 Drawing Sheets

OTHER PUBLICATIONS

Hamel et al., "Phenotype and Function of Bone Marrow-–Derived T–and Non–T–Cells Activated in Vitro By Alpha–Fetoprotein," In: Biological Activities of Alpha–Fetoprotein (vol. 1), Mizejewski, G.J. and Jacobson, H.I (eds.), CRC Press, Inc. (Boca Raton, Fl), pp. 167–177 (1987).

Heyward et al., "Early Detection Of Primary Hepatocellular Carcinoma By Screening For Alpha–Fetoprotein In High-–Risk Families," The Lancet 2:1161–1162 (1983).

Hooper et al., "Human AFP Inhibits Cell Proliferation and NK–Like Cytotoxic Activity Generated in Autologous, But Not In Allogeneic Mixed Lymphocyte Reactions," In: Biological Activities of Alpha–Fetoprotein, (vol. II) Mizejewski, G.J. and Jacobson, H.I. (eds.), CRC Press, Inc. (Boca Raton, FL), pp. 183–197 (1989).

Hooper et al., "Selective Inhibition Of Murine T–Cell Proliferation And Lymphokine–Activated Natural Killer Cell Function By alpha–Fetoprotein, In: Biological Activities of Alpha–Fetoprotein," (vol. 1) Mizejewski, G.J. and Jacobson, H.I (eds.), CRC Press, Inc. (Boca Raton, FL), pp. 153–165 (1987).

Hooper et al., "Regulation of Murine T–Cell Responses to Autologous Antigens by α–Fetoprotein," Cellular Immunology 63:417–425 (1981).

Hooper et al., "Suppression Of Primary And Secondary Autologous Mixed Lymphocyte Reactions By Murine Alphafetoprotein," Oncodevelopmental Biology and Medicine 3:151–160 (1982).

Hoskin et al., "Analysis of Pregnancy–Associated Immunoregulatory Pathways," In: Alpha–Fetoprotein and Congenital Disorders, Academic Press, Inc. (New York), pp. 59–78 (1985).

Hoskin et al., "In Vitro Activation of Bone Marrow–Derived T–and Non–T–Cells Subsets by α–Fetoprotein," Cellular Immunology 96:163–174 (1985).

Hoskin et al., "Specific Maternal Anti–fetal Lymphoproliferative Responses And Their Regulation By Natural Immunosuppressive Factors," Clin. Exp. Immunol. 76:262–267 (1989).

Innis et al., "Amplification of α–Fetoprotein Complementary DNA by Insertion into a Bacterial Plasmid," Archives of Biochemistry and Biophysics 195:128–135 (1979).

Ishiguro et al., "Serum Alpha–Fetoprotein Subfractions in Patients With Primary Hepatoma or Hepatic Metastasis of Gastric Cancer," Cancer 55:156–159 (1985).

Jacobson et al., "Inhibition of Estrogen–dependent Breast Cancer Growth by a Reaction Product of α–Fetoprotein and Estradiol," Cancer Research 50:415–420 (1990).

Jiang et al., "Role of CD8$^+$T Cells In Murine Experimental Allergic Encephalomyelitis," Science 256:1213–1215 (1992).

Keller et al., "Immunosuppressive Properties of AFP: Role Of Estrogens," In: Onco–Developmental Gene Expression, Fishman, W.H. and Sell, S. (eds.), Academic Press, Inc. (New York) pp. 287–295 (1976).

Kikutani et al., "The Murine Autoimmune Diabetes Model: NOD and Related Strains," Advances in Immunology 51:285–322 (1992).

Line et al., "Medical Potential Of AFP As A Tumor Imaging Agent," In: Biological Activities of Alpha–Fetoprotein (vol. II), Mizejewski, G.J. and Jacobson, H.I (eds.), CRC Press, Inc. (Boca Raton, FL), pp. 139–148 (1989).

Lu et al., "α–Fetoprotein Inhibits Macrophage Expressions Of la Antigens," The Journal of Immunology 132:1722–1727 (1984).

Masuda et al., "Selective Antitumor Effect of Thioether-–Linked Immunotoxins Composed of Gelonin and Monoclonal Antibody to Alpha–Fetoprotein or its F(ab')$_2$ Fragment," Tumor Biol. 15:175–183 (1994).

Mizejewski et al., "Alpha Fetoprotein Testing: Regulatory and Technical Considerations," Laboratory Management (1987).

Morinaga et al., "Primary Structures Of Human α–fetoprotein And Its mRNA," Proc. Natl. Acad. Sci. USA 80:4604–4608 (1983).

Moro et al., "Monoclonal Antibodies Directed against a Widespread Oncofetal Antigen: The Alpha–Fetoprotein Receptor," Tumor Biol. 14:116–130 (1993).

Murgita et al., "Selective Immunoregulatory Properties Of α–Fetoprotein," La Ricerca Clin. Lab. 9:327–342 (1979).

Murgita et al., "Regulation of Immune Functions in the Fetus and Newborn," Progress Allergy 29:54–132 (1981).

Murgita et al., "Suppression Of The Immune Response By α–Fetoprotein," The Journal of Experimental Medicine 141:440–452 (1975).

Murgita et al., "Suppression Of The Immune Response By α–Fetoprotein," The Journal of Experimental Medicine 141:269–286 (1975).

Murgita et al., "Adult murine T cells activated in vitro by α–fetoprotein and naturally occuring T cells in newborn mice: Identity in function and cell surface differentiation antigens," Proc. Natl. Acad. Sci. USA 75:2897–2901 (1978).

Murgita et al., "Effects of human alpha–foetoprotein on human B and T lymphocyte proliferaton in vitro," Clin. Exp. Immunol. 33:347–356 (1978).

Murgita et al., "The Effects of Mouse Alpha–Fetoprotein on T–Cell–Dependent and T–Cell–Independent Immune Responses In Vitro," Scand. J. Immunol. 5:1215–1220 (1976).

Murgita et al., "The Immunosuppressive Role of Alpha–Feto–protein During Pregnancy," Scand. J. Immunol. 5:1003–1014 (1976).

Murgita et al., "α–Fetoprotein induces suppressor T cells in vitro," Nature 267:257–258 (1977).

Murgita et al., "Characterization Of Murine Newborn Inhibitory T Lymphocytes: Functional And Phenotype Comparison With An Adult T Subset Activated in vitro By Alpha–fetoprotein," Eur. J. Immunol. 11:957–964 (1981).

Nelson et al., "Maternal–Fetal Disparity in HLA Class II Alloantigens And The Pregnancy–Induced Amelioration of Rheumatoid Arthritis," The New England Journal of Medicine 329:466–471 (1993).

Nishi et al., "Expression of Rat α–Fetoprotein cDNA in *Escherichia coli* and in Yeast," J. Biochem. 104:968–972 (1988).

O'Neill et al., "Regulation Of Human Lymphocyte Activation By Alpha–Fetoprotein: Evidence For Selective Suppression Of la–Associated T–Cell Proliferation In Vitro," Oncodevelopmental Biology and Medicine 3:135–150 (1982).

Peck et al., "Cellular And Genetic Restrictions In The Immunoregulatory Activity Of α–Fetoprotein," The Journal of Immunology 128:1134–1140 (1982).

Peck et al., "Cellular And Genetic Restrictions In The Immunoregulatory Activity Of Alpha–Fetoprotein," The Journal of Experimental Medicine 147:667–683 (1978).

Peck et al., "Cellular And Genetic Restrictions In The Immunoregulatory Activity Of Alph–Fetoprotein," J. Exp. Med. 148:360–372 (1978)..

Sell, "Alphafetoprotein," In: Cancer Markers Diagnostic and Developmental Significance, Sell, S., (ed.), Humana Press, Clifton, NJ pp. 249–293 (1980).

Semeniuk et al., "Immunoregulation By Recombinant Alpha–Fetoproteins Produced In Eukaryotic And Prokaryotic Expression Systems," Abstracts 2799, Experimental Biology 94™, Anaheim, CA (1994).

Soto et al., "Control Of Growth Of Estrogen–sensitive Cells: Role For α–fetoprotein," Proc. Natl. Acad. Acad. Sci. USA 77:2084–2087 (1980).

van Oers et al., "Analytical– And Preparative–Scale Separation Of Molecular Variants of α–Fetoprotein By Anion–Exchange Chromatography On Monobead™ Resins,"Journal of Chromatography 525:59–69 (1990).

van Oers et al., "Isolation And Characterization Of A Distinct Immunoregulatory Isoform Of α–Fetoprotein Produced By The Normal Fetus," J. Exp. Med. 170:811–825 (1989).

Villacampa et al., "Alpha–Fetoprotein Receptors In A Human Breast Cancer Cell Line," Biochemical and Biophysical Research Communications 122:1322–1327 (1984).

```
                                                                              AT    (2)
                                                                              -1
                    -19                              -10
                    met lys trp val glu ser ile phe leu ile phe leu leu asn phe thr glu ser arg
                    ATG AAG TGG GTG GAA TCA ATT TTT TTA ATT TTC CTA AAT TTT ACT GAA TCC AGA  (101)
ATTGTGCTTCCACTACTGCCAATAACAAAATAACTAGCAACC
              10                           20                          30
  1   thr leu his arg asn glu tyr gly ile ala ser ile leu asp ser tyr gln cys thr ala glu ile ser leu ala asp leu ala thr ile
      ACA CTG CAT AGA AAT GAA TAT GGA ATA GCT TCC ATA TTG GAT TCT TAC CAA TGT ACT GCA GAG ATA AGT CTT GAT GCT TTA GCT ACC ATA  (191)
              40                           50                          60
 31   phe phe ala gln phe val gln glu ala thr tyr lys glu val ser lys met val lys glu lys met asp ala leu thr ala ile glu lys pro thr gly
      TTT TTT GCC CAG TTT GTT CAA GAA GCC ACT TAC AAG GAA GTA AGC AAA ATG GTG AAA GAA AAG ATG GAT GCA TTA ACT GCA ATT GAG AAA CCC ACT GGA  (281)
              70                           80                          90
 61   asp glu gln ser ser gly cys leu glu asn gln leu pro ala phe leu glu glu leu cys his glu leu cys lys ile leu glu lys tyr gly
      GAT GAA GAG TCT TCA GGG TGT TTA GAA AAC CAG CTA CCT GCC TTT CTG GAA GAA CTT TGC CAT GAG CTT TGC AAA ATT TTG GAG AAG TAC GGA  (371)
              100                          110                         120
 91   his ser asp cys cys ser ser gln ser glu gly gly arg his asn cys phe leu ala his lys lys pro thr pro ala ser ile pro leu phe
      CAT TCA GAC TGC TGC AGC AGT CAG AGT GAA GAG GGA AGA CAT AAC TGT TTT CTT GCA CAC AAA AAG CCC ACT CCA GCA TCG ATC CCA CTT TTC  (461)
              130                          140                         150
121   gln val pro glu pro val thr ser cys glu ala tyr glu glu asp arg glu thr phe met asn lys phe ile tyr glu ile ala arg arg
      CAA GTT CCA GAA CCT GTC ACA AGC TGT GAA GCA TAT GAA GAA GAC AGG GAG ACA TTC ATG AAT AAA TTC ATT TAT GAG ATA GCA AGA AGG  (551)
              160                          170                         180
151   his pro phe leu tyr ala pro thr ile leu leu trp ala ala arg tyr asp lys ile ile pro ser cys cys lys ala glu asn ala val
      CAT CCC TTC CTG TAT GCA CCT ACA ATT CTT CTT TGG GCT GCT CGC TAT GAC AAA ATA ATT CCA TCT TGC TGC AAA GCT GAA AAT GCA GTT  (641)
              190                          200                         210
181   glu cys phe gln thr lys ala ala thr val thr lys leu arg glu leu arg ser ser leu leu asn gln his ala cys ala val met lys asn
      GAA TGC TTC CAA ACA AAG GCA GCA ACA GTT ACA AAA GAA TTA AGA GAA CTG AGA AGC AGT TTA AAT CAA CAT GCA TGT GCA GTA ATG AAA AAT  (731)

Fig. 4-1
```

```
211 phe gly thr arg thr phe gln ala ile thr val thr lys leu ser gln lys phe thr lys val asn phe thr glu ile gln lys leu val 240
    TTT GGG ACC CGA ACT TTC CAA GCC ATA ACT GTT ACT AAA CTG AGT CAG AAG TTT ACC AAA GTT AAT TTT ACT GAA ATC CAG AAA CTA GTC (821)

241 leu asp val ala his val his glu his cys cys arg gly asp val leu asp cys lys leu thr thr leu glu cys gln asp gly glu lys ile met ser tyr ile cys 270
    CTG GAT GTG GCC CAT GTA CAT GAG CAC TGT TGC AGA GGA GAT GTG CTG GAT TGT AAA CTG ACC ACG CTG GAA TGT CAG GAT GGA GAA AAA ATC ATG TCC TAC ATA TGT (911)

271 ser gln gln asp thr leu ser asn lys ile thr glu cys cys ile thr glu arg gly gln cys ile ile his ala glu asn 300
    TCT CAA CAA GAC ACT CTG TCA AAC AAA ATA ACA GAA TGC TGC ATA ACT GAA CGT GGT CAA TGT ATA ATT CAT GCA GAA AAT (1001)

301 asp glu lys pro glu gly leu ser pro asn leu asn arg phe leu gly asp arg asp phe ser gln phe ser ser gly lys lys asn ile 330
    GAT GAA AAA CCT GAA GGT CTA TCT CCA AAT CTA AAC AGG TTT TTA GGA GAT AGA GAT TTC AAC CAA TTT TCT TCA GGG AAA AAT ATC (1091)

331 phe leu ala ser phe val his glu tyr ser arg arg his pro gln leu ala val ser val ile leu arg val ala lys gly tyr ile gln glu 360
    TTC TTG GCA AGT TTT GTT CAT GAA TAT TCA AGA AGA CAT CCT CAG CTT GCT GTC TCA ATT CTA AGA GTT GCT AAA GGA TAC ATC CAG GAG (1181)

361 leu leu glu lys cys phe gln thr glu asn pro leu glu cys gln asp lys lys leu gln leu lys tyr ile gln leu glu ser gln 390
    TTA TTG GAG AAG TGT TTC CAG ACT GAA AAC CCT CTT GAA TGC CAA GAT AAA AAG CTA CAG TTA AAG TAC ATC CAG TTA GAG AGC CAA (1271)

391 ala leu ala lys ser arg cys gly leu phe gln lys leu gly glu tyr tyr leu gln asn ala phe leu val ala tyr thr lys lys ala 420
    GCA TTG GCA AAG CGA AGC TGC GGC CTC TTC CAG AAA CTA GGA GAA TAT TAC TTA CAA AAT GCG TTT CTC GTT GCT TAC ACA AAG AAA GCC (1361)

421 pro gln leu thr ser ser glu leu met ala ile thr arg lys met ala ala thr ala ala cys cys gln leu ser glu asp lys leu 450
    CCC CAG CTG ACC TCG TCG GAG CTG ATG GCA ATC ACC AGA AAA ATG GCA GCC ACA GCA GCC ACT TGT TGC CAA CTC AGT GAG GAC AAA CTA (1451)
```

Fig. 4-2

```
451
leu ala cys gly gly ala ala asp ile ile gly his leu cys ile arg his glu met thr pro val asn pro gly val gly gln       480
TTG GCC TGT GGC GAG GGA GCG GCT ATT ATC GGA CAC TTA TGT ATC AGA CAT GAA ATG ACT CCA GTA AAC CCT GGT GTT GGC CAG(1541)

481
cys cys thr ser tyr ala asn arg pro cys phe ser ser leu val val asp glu thr tyr val pro pro ala phe ser asp          510
TGC TGC ACT TCT TCA TAT GCC AAC AGG CCA TGC TTC AGC AGC TTG GTG GTG GAT GAA ACA TAT GTC CCT CCT GCA TTC TCT GAC(1631)

511
lys phe ile phe his lys asp leu cys gln ala gln gly val ala leu gln thr met lys gln glu phe leu ile asn leu val lys gln  540
AAG TTC ATT TTC CAT AAG GAT CTG TGC CAA GCT CAG GGT GTA GCG CTG CAA ACG ATG AAG CAA GAG TTT CTC ATT AAC CTT GTG AAG CAA(1721)

541
lys pro gln ile thr glu glu gln leu glu ala val ile ala asp phe ser gly leu leu glu lys cys cys gln gln gly gln gln glu  570
AAG CCA CAA ATA ACA GAG GAA CAA CTT GAG GCT GTC ATT GCA GAT TTC TCA GGC TTG CTG GAG AAA TGC TGC CAA CAG GGA CAG CAG GAA(1811)

571
val cys phe ala glu glu gly gln lys leu ile ser lys thr arg ala ala leu gly val ter                                    590
GTC TGC TTT GCT GAA GAG GGA CAA AAA CTG ATT TCA AAA ACT CGT GCT GCT TTG GGA GTT TAA ATTACTTCAGGGGAAGAAGACAAAACGAGTCT(1908)

TTCATTCGGTGTGAACTTTTCTCTTAATTTAACTGATTTAACACTTTTTGTGAATTAATGAAATGATAAAGACTTTATGTGAGATTTCCTTATCACAGAAATAAATATCTCCAAA(2027)
```

Fig. 4-3

SEQUENCE LISTING

<160> NUMBER OF SEQ ID NOS: 16

<210> SEQ ID NO 1
<211> LENGTH: 2027
<212> TYPE: DNA
<213> ORGANISM: Homo sapiens

<400> SEQUENCE: 1

```
atattgtgct tccaccactg ccaataacaa ataaactagc aaccatgaag tgggtggaat      60
caattttttt aattttccta ctaaatttta ctgaatccag aacactgcat agaaatgaat     120
atggaatagc ttccatattg gattcttacc aatgtactgc agagataagt ttagctgacc     180
tggctaccat attttttgcc cagtttgttc aagaagccac ttacaaggaa gtaagcaaaa     240
tggtgaaaga tgcattgact gcaattgaga aacccactgg agatgaacag tcttcagggt     300
gtttagaaaa ccagctacct gcctttctgg aagaactttg ccatgagaaa gaaattttgg     360
agaagtacgg acattcagac tgctgcagcc aaagtgaaga gggaagacat aactgttttc     420
ttgcacacaa aaagcccact gcagcatgga tcccactttt ccaagttcca gaacctgtca     480
caagctgtga agcatatgaa gaagacaggg agacattcat gaacaaattc atttatgaga     540
tagcaagaag gcatccctttc ctgtatgcac ctacaattct tctttcggct gctgggtatg     600
agaaaataat tccatcttgc tgcaaagctg aaaatgcagt tgaatgcttc caaacaaagg     660
cagcaacagt tacaaaagaa ttaagagaaa gcagcttgtt aaatcaacat gcatgtccag     720
taatgaaaaa ttttgggacc cgaactttcc aagccataac tgttactaaa ctgagtcaga     780
agtttaccaa agttaatttt actgaaatcc agaaactagt cctggatgtg gcccatgtac     840
atgagcactg ttgcagagca gatgtgctgg attgtctgca ggatggggaa aaaatcatgt     900
cctacatatg ttctcaacaa gacactctgt caaacaaaat aacagaatgc tgcaaactga     960
ccacgctgga acgtggtcaa tgtataattc atgcagaaaa tgatgaaaaa cctgaaggtc    1020
tatctccaaa tctaaacagg tttttaggag atagagattt taaccaattt tcttcagggg    1080
aaaaaaatat cttcttggca agttttgttc atgaatattc aagaagacat cctcagcttg    1140
ctgtctcagt aattctaaga gttgctaaag gataccagga gttattggag aagtgtttcc    1200
agactgaaaa ccctcttgaa tgccaagata aggagaaga agaattacag aaatacatcc    1260
aggagagcca agcattggca aagcgaagct gcggcctctt ccagaaacta ggagaatatt    1320
acttacaaaa tgagtttctc gttgcttaca caaagaaagc cccccagctg acctcgtcgg    1380
agctgatggc catcaccaga aaaatggcag ccacagcagc cacttgttgc caactcagtg    1440
aggacaaact attggcctgt ggcgagggag cggctgacat tattatcgga cacttatgta    1500
tcagacatga aatgactcca gtaaaccctg gtgttggcca gtgctgcact tcttcatatg    1560
ccaacaggag gccatgcttc agcagcttgg tggtggatga acatatgtc cctcctgcat    1620
tctctgatga caagttcatt ttccataagg atctgtgcca agctcagggt gtagcgctgc    1680
aaaggatgaa gcaagagttt ctcattaacc ttgtgaagca aaagccacaa ataacagagg    1740
aacaacttga ggctctcatt gcagatttct caggcctgtt ggagaaatgc tgccaaggcc    1800
```

```
aggaacagga agtctgcttt gctgaagagg gacaaaaact gatttcaaaa actggtgctg    1860
ctttgggagt ttaaattact tcaggggaag agaagacaaa acgagtcttt cattcggtgt    1920
gaacttttct ctttaatttt aactgattta acacttttg tgaattaatg aaatgataaa    1980 gactttatg tgagatttcc ttatcacaga aataaaatat ctccaaa                  2027
```

<210> SEQ ID NO 2
<211> LENGTH: 590
<212> TYPE: PRT
<213> ORGANISM: Homo sapiens

<400> SEQUENCE: 2

```
Thr Leu His Arg Asn Glu Tyr Gly Ile Ala Ser Ile Leu Asp Ser Tyr
 1               5                   10                  15

Gln Cys Thr Ala Glu Ile Ser Leu Ala Asp Leu Ala Thr Ile Phe Phe
            20                  25                  30

Ala Gln Phe Val Gln Glu Ala Thr Tyr Lys Glu Val Ser Lys Met Val
        35                  40                  45

Lys Asp Ala Leu Thr Ala Ile Glu Lys Pro Thr Gly Asp Glu Gln Ser
    50                  55                  60

Ser Gly Cys Leu Glu Asn Gln Leu Pro Ala Phe Leu Glu Glu Leu Cys
65                  70                  75                  80

His Glu Lys Glu Ile Leu Glu Lys Tyr Gly His Ser Asp Cys Cys Ser
                85                  90                  95

Gln Ser Glu Glu Gly Arg His Asn Cys Phe Leu Ala His Lys Lys Pro
            100                 105                 110

Thr Ala Ala Trp Ile Pro Leu Phe Gln Val Pro Glu Pro Val Thr Ser
        115                 120                 125

Cys Glu Ala Tyr Glu Glu Asp Arg Glu Thr Phe Met Asn Lys Phe Ile
    130                 135                 140

Tyr Glu Ile Ala Arg Arg His Pro Phe Leu Tyr Ala Pro Thr Ile Leu
145                 150                 155                 160

Leu Ser Ala Ala Gly Tyr Glu Lys Ile Ile Pro Ser Cys Cys Lys Ala
                165                 170                 175

Glu Asn Ala Val Glu Cys Phe Gln Thr Lys Ala Ala Thr Val Thr Lys
            180                 185                 190

Glu Leu Arg Glu Ser Ser Leu Leu Asn Gln His Ala Cys Pro Val Met
        195                 200                 205

Lys Asn Phe Gly Thr Arg Thr Phe Gln Ala Ile Thr Val Thr Lys Leu
    210                 215                 220

Ser Gln Lys Phe Thr Lys Val Asn Phe Thr Glu Ile Gln Lys Leu Val
225                 230                 235                 240

Leu Asp Val Ala His Val His Glu His Cys Cys Arg Ala Asp Val Leu
                245                 250                 255

Asp Cys Leu Gln Asp Gly Glu Lys Ile Met Ser Tyr Ile Cys Ser Gln
            260                 265                 270

Gln Asp Thr Leu Ser Asn Lys Ile Thr Glu Cys Cys Lys Leu Thr Thr
        275                 280                 285

Leu Glu Arg Gly Gln Cys Ile Ile His Ala Glu Asn Asp Glu Lys Pro
    290                 295                 300

Glu Gly Leu Ser Pro Asn Leu Asn Arg Phe Leu Gly Asp Arg Asp Phe
305                 310                 315                 320

Asn Gln Phe Ser Ser Gly Glu Lys Asn Ile Phe Leu Ala Ser Phe Val
                325                 330                 335
```

His Glu Tyr Ser Arg Arg His Pro Gln Leu Ala Val Ser Val Ile Leu
            340                 345                 350

Arg Val Ala Lys Gly Tyr Gln Glu Leu Leu Glu Lys Cys Phe Gln Thr
            355                 360                 365

Glu Asn Pro Leu Glu Cys Gln Asp Lys Gly Glu Glu Glu Leu Gln Lys
            370                 375                 380

Tyr Ile Gln Glu Ser Gln Ala Leu Ala Lys Arg Ser Cys Gly Leu Phe
385                 390                 395                 400

Gln Lys Leu Gly Glu Tyr Tyr Leu Gln Asn Glu Phe Leu Val Ala Tyr
            405                 410                 415

Thr Lys Lys Ala Pro Gln Leu Thr Ser Ser Glu Leu Met Ala Ile Thr
            420                 425                 430

Arg Lys Met Ala Ala Thr Ala Ala Thr Cys Cys Gln Leu Ser Glu Asp
            435                 440                 445

Lys Leu Leu Ala Cys Gly Glu Gly Ala Ala Asp Ile Ile Ile Gly His
            450                 455                 460

Leu Cys Ile Arg His Glu Met Thr Pro Val Asn Pro Gly Val Gly Gln
465                 470                 475                 480

Cys Cys Thr Ser Ser Tyr Ala Asn Arg Arg Pro Cys Phe Ser Ser Leu
            485                 490                 495

Val Val Asp Glu Thr Tyr Val Pro Pro Ala Phe Ser Asp Asp Lys Phe
            500                 505                 510

Ile Phe His Lys Asp Leu Cys Gln Ala Gln Gly Val Ala Leu Gln Arg
            515                 520                 525

Met Lys Gln Glu Phe Leu Ile Asn Leu Val Lys Gln Lys Pro Gln Ile
            530                 535                 540

Thr Glu Glu Gln Leu Glu Ala Leu Ile Ala Asp Phe Ser Gly Leu Leu
545                 550                 555                 560

Glu Lys Cys Cys Gln Gly Gln Glu Gln Glu Val Cys Phe Ala Glu Glu
            565                 570                 575

Gly Gln Lys Leu Ile Ser Lys Thr Gly Ala Ala Leu Gly Val
            580                 585                 590

<210> SEQ ID NO 3
<211> LENGTH: 197
<212> TYPE: PRT
<213> ORGANISM: Homo sapiens

<400> SEQUENCE: 3

Thr Leu His Arg Asn Glu Tyr Gly Ile Ala Ser Ile Leu Asp Ser Tyr
1               5                   10                  15

Gln Cys Thr Ala Glu Ile Ser Leu Ala Asp Leu Ala Thr Ile Phe Phe
            20                  25                  30

Ala Gln Phe Val Gln Glu Ala Thr Tyr Lys Glu Val Ser Lys Met Val
            35                  40                  45

Lys Asp Ala Leu Thr Ala Ile Glu Lys Pro Thr Gly Asp Glu Gln Ser
            50                  55                  60

Ser Gly Cys Leu Glu Asn Gln Leu Pro Ala Phe Leu Glu Glu Leu Cys
65                  70                  75                  80

His Glu Lys Glu Ile Leu Glu Lys Tyr Gly His Ser Asp Cys Cys Ser
            85                  90                  95

Gln Ser Glu Glu Gly Arg His Asn Cys Phe Leu Ala His Lys Lys Pro
            100                 105                 110

Thr Ala Ala Trp Ile Pro Leu Phe Gln Val Pro Glu Pro Val Thr Ser
            115                 120                 125

```
Cys Glu Ala Tyr Glu Asp Arg Glu Thr Phe Met Asn Lys Phe Ile
    130                 135                 140

Tyr Glu Ile Ala Arg Arg His Pro Phe Leu Tyr Ala Pro Thr Ile Leu
145                 150                 155                 160

Leu Ser Ala Ala Gly Tyr Glu Lys Ile Ile Pro Ser Cys Cys Lys Ala
                165                 170                 175

Glu Asn Ala Val Glu Cys Phe Gln Thr Lys Ala Ala Thr Val Thr Lys
                180                 185                 190

Glu Leu Arg Glu Ser
            195
```

<210> SEQ ID NO 4
<211> LENGTH: 192
<212> TYPE: PRT
<213> ORGANISM: Homo sapiens

<400> SEQUENCE: 4

```
Ser Leu Leu Asn Gln His Ala Cys Pro Val Met Lys Asn Phe Gly Thr
1               5                   10                  15

Arg Thr Phe Gln Ala Ile Thr Val Thr Lys Leu Ser Gln Lys Phe Thr
                20                  25                  30

Lys Val Asn Phe Thr Glu Ile Gln Lys Leu Val Leu Asp Val Ala His
                35                  40                  45

Val His Glu His Cys Cys Arg Ala Asp Val Leu Asp Cys Leu Gln Asp
            50                  55                  60

Gly Glu Lys Ile Met Ser Tyr Ile Cys Ser Gln Gln Asp Thr Leu Ser
65                  70                  75                  80

Asn Lys Ile Thr Glu Cys Cys Lys Leu Thr Thr Leu Glu Arg Gly Gln
                85                  90                  95

Cys Ile Ile His Ala Glu Asn Asp Glu Lys Pro Glu Gly Leu Ser Pro
                100                 105                 110

Asn Leu Asn Arg Phe Leu Gly Asp Arg Asp Phe Asn Gln Phe Ser Ser
            115                 120                 125

Gly Glu Lys Asn Ile Phe Leu Ala Ser Phe Val His Glu Tyr Ser Arg
130                 135                 140

Arg His Pro Gln Leu Ala Val Ser Val Ile Leu Arg Val Ala Lys Gly
145                 150                 155                 160

Tyr Gln Glu Leu Leu Glu Lys Cys Phe Gln Thr Glu Asn Pro Leu Glu
                165                 170                 175

Cys Gln Asp Lys Gly Glu Glu Leu Gln Lys Tyr Ile Gln Glu Ser
                180                 185                 190
```

<210> SEQ ID NO 5
<211> LENGTH: 201
<212> TYPE: PRT
<213> ORGANISM: Homo sapiens

<400> SEQUENCE: 5

```
Gln Ala Leu Ala Lys Arg Ser Cys Gly Leu Phe Gln Lys Leu Gly Glu
1               5                   10                  15

Tyr Tyr Leu Gln Asn Glu Phe Leu Val Ala Tyr Thr Lys Lys Ala Pro
                20                  25                  30

Gln Leu Thr Ser Ser Glu Leu Met Ala Ile Thr Arg Lys Met Ala Ala
            35                  40                  45

Thr Ala Ala Thr Cys Cys Gln Leu Ser Glu Asp Lys Leu Leu Ala Cys
50                  55                  60
```

```
Gly Glu Gly Ala Ala Asp Ile Ile Ile Gly His Leu Cys Ile Arg His
 65                  70                  75                  80

Glu Met Thr Pro Val Asn Pro Gly Val Gly Gln Cys Cys Thr Ser Ser
                 85                  90                  95

Tyr Ala Asn Arg Arg Pro Cys Phe Ser Ser Leu Val Val Asp Glu Thr
            100                 105                 110

Tyr Val Pro Pro Ala Phe Ser Asp Asp Lys Phe Ile Phe His Lys Asp
        115                 120                 125

Leu Cys Gln Ala Gln Gly Val Ala Leu Gln Arg Met Lys Gln Glu Phe
    130                 135                 140

Leu Ile Asn Leu Val Lys Gln Lys Pro Gln Ile Thr Glu Glu Gln Leu
145                 150                 155                 160

Glu Ala Leu Ile Ala Asp Phe Ser Gly Leu Leu Glu Lys Cys Cys Gln
                165                 170                 175

Gly Gln Glu Gln Glu Val Cys Phe Ala Glu Glu Gly Gln Lys Leu Ile
            180                 185                 190

Ser Lys Thr Gly Ala Ala Leu Gly Val
        195                 200
```

<210> SEQ ID NO 6
<211> LENGTH: 389
<212> TYPE: PRT
<213> ORGANISM: Homo sapiens

<400> SEQUENCE: 6

```
Thr Leu His Arg Asn Glu Tyr Gly Ile Ala Ser Ile Leu Asp Ser Tyr
  1               5                  10                  15

Gln Cys Thr Ala Glu Ile Ser Leu Ala Asp Leu Ala Thr Ile Phe Phe
             20                  25                  30

Ala Gln Phe Val Gln Glu Ala Thr Tyr Lys Glu Val Ser Lys Met Val
         35                  40                  45

Lys Asp Ala Leu Thr Ala Ile Glu Lys Pro Thr Gly Asp Glu Gln Ser
 50                  55                  60

Ser Gly Cys Leu Glu Asn Gln Leu Pro Ala Phe Leu Glu Glu Leu Cys
 65                  70                  75                  80

His Glu Lys Glu Ile Leu Glu Lys Tyr Gly His Ser Asp Cys Cys Ser
                 85                  90                  95

Gln Ser Glu Glu Gly Arg His Asn Cys Phe Leu Ala His Lys Lys Pro
            100                 105                 110

Thr Ala Ala Trp Ile Pro Leu Phe Gln Val Pro Glu Pro Val Thr Ser
        115                 120                 125

Cys Glu Ala Tyr Glu Glu Asp Arg Glu Thr Phe Met Asn Lys Phe Ile
    130                 135                 140

Tyr Glu Ile Ala Arg Arg His Pro Phe Leu Tyr Ala Pro Thr Ile Leu
145                 150                 155                 160

Leu Ser Ala Ala Gly Tyr Glu Lys Ile Ile Pro Ser Cys Cys Lys Ala
                165                 170                 175

Glu Asn Ala Val Glu Cys Phe Gln Thr Lys Ala Ala Thr Val Thr Lys
            180                 185                 190

Glu Leu Arg Glu Ser Ser Leu Leu Asn Gln His Ala Cys Pro Val Met
        195                 200                 205

Lys Asn Phe Gly Thr Arg Thr Phe Gln Ala Ile Thr Val Thr Lys Leu
    210                 215                 220

Ser Gln Lys Phe Thr Lys Val Asn Phe Thr Glu Ile Gln Lys Leu Val
```

-continued

```
                225                 230                 235                 240

Leu Asp Val Ala His Val His Glu His Cys Cys Arg Ala Asp Val Leu
                245                 250                 255

Asp Cys Leu Gln Asp Gly Glu Lys Ile Met Ser Tyr Ile Cys Ser Gln
                260                 265                 270

Gln Asp Thr Leu Ser Asn Lys Ile Thr Glu Cys Cys Lys Leu Thr Thr
                275                 280                 285

Leu Glu Arg Gly Gln Cys Ile Ile His Ala Glu Asn Asp Glu Lys Pro
                290                 295                 300

Glu Gly Leu Ser Pro Asn Leu Asn Arg Phe Leu Gly Asp Arg Asp Phe
305                 310                 315                 320

Asn Gln Phe Ser Ser Gly Glu Lys Asn Ile Phe Leu Ala Ser Phe Val
                325                 330                 335

His Glu Tyr Ser Arg Arg His Pro Gln Leu Ala Val Ser Val Ile Leu
                340                 345                 350

Arg Val Ala Lys Gly Tyr Gln Glu Leu Leu Glu Lys Cys Phe Gln Thr
                355                 360                 365

Glu Asn Pro Leu Glu Cys Gln Asp Lys Gly Glu Glu Leu Gln Lys
                370                 375                 380

Tyr Ile Gln Glu Ser
385
```

<210> SEQ ID NO 7
<211> LENGTH: 393
<212> TYPE: PRT
<213> ORGANISM: Homo sapiens

<400> SEQUENCE: 7

```
Ser Leu Leu Asn Gln His Ala Cys Pro Val Met Lys Asn Phe Gly Thr
1                   5                   10                  15

Arg Thr Phe Gln Ala Ile Thr Val Thr Lys Leu Ser Gln Lys Phe Thr
                20                  25                  30

Lys Val Asn Phe Thr Glu Ile Gln Lys Leu Val Leu Asp Val Ala His
                35                  40                  45

Val His Glu His Cys Cys Arg Ala Asp Val Leu Asp Cys Leu Gln Asp
                50                  55                  60

Gly Glu Lys Ile Met Ser Tyr Ile Cys Ser Gln Gln Asp Thr Leu Ser
65                  70                  75                  80

Asn Lys Ile Thr Glu Cys Cys Lys Leu Thr Thr Leu Glu Arg Gly Gln
                85                  90                  95

Cys Ile Ile His Ala Glu Asn Asp Glu Lys Pro Glu Gly Leu Ser Pro
                100                 105                 110

Asn Leu Asn Arg Phe Leu Gly Asp Arg Asp Phe Asn Gln Phe Ser Ser
                115                 120                 125

Gly Glu Lys Asn Ile Phe Leu Ala Ser Phe Val His Glu Tyr Ser Arg
                130                 135                 140

Arg His Pro Gln Leu Ala Val Ser Val Ile Leu Arg Val Ala Lys Gly
145                 150                 155                 160

Tyr Gln Glu Leu Leu Glu Lys Cys Phe Gln Thr Glu Asn Pro Leu Glu
                165                 170                 175

Cys Gln Asp Lys Gly Glu Glu Leu Gln Lys Tyr Ile Gln Glu Ser
                180                 185                 190

Gln Ala Leu Ala Lys Arg Ser Cys Gly Leu Phe Gln Lys Leu Gly Glu
                195                 200                 205
```

-continued

```
Tyr Tyr Leu Gln Asn Glu Phe Leu Val Ala Tyr Thr Lys Lys Ala Pro
    210                 215                 220
Gln Leu Thr Ser Ser Glu Leu Met Ala Ile Thr Arg Lys Met Ala Ala
225                 230                 235                 240
Thr Ala Ala Thr Cys Cys Gln Leu Ser Glu Asp Lys Leu Leu Ala Cys
                245                 250                 255
Gly Glu Gly Ala Ala Asp Ile Ile Ile Gly His Leu Cys Ile Arg His
                260                 265                 270
Glu Met Thr Pro Val Asn Pro Val Gly Gln Cys Cys Thr Ser Ser
                275                 280                 285
Tyr Ala Asn Arg Arg Pro Cys Phe Ser Ser Leu Val Val Asp Glu Thr
    290                 295                 300
Tyr Val Pro Pro Ala Phe Ser Asp Asp Lys Phe Ile Phe His Lys Asp
305                 310                 315                 320
Leu Cys Gln Ala Gln Gly Val Ala Leu Gln Arg Met Lys Gln Glu Phe
                325                 330                 335
Leu Ile Asn Leu Val Lys Gln Lys Pro Gln Ile Thr Glu Glu Gln Leu
                340                 345                 350
Glu Ala Leu Ile Ala Asp Phe Ser Gly Leu Leu Glu Lys Cys Cys Gln
                355                 360                 365
Gly Gln Glu Gln Glu Val Cys Phe Ala Glu Glu Gly Gln Lys Leu Ile
    370                 375                 380
Ser Lys Thr Gly Ala Ala Leu Gly Val
385                 390

<210> SEQ ID NO 8
<211> LENGTH: 325
<212> TYPE: PRT
<213> ORGANISM: Homo sapiens

<400> SEQUENCE: 8

Met Ser Tyr Ile Cys Ser Gln Gln Asp Thr Leu Ser Asn Lys Ile Thr
1               5                   10                  15
Glu Cys Cys Lys Leu Thr Thr Leu Glu Arg Gly Gln Cys Ile Ile His
                20                  25                  30
Ala Glu Asn Asp Glu Lys Pro Glu Gly Leu Ser Pro Asn Leu Asn Arg
            35                  40                  45
Phe Leu Gly Asp Arg Asp Phe Asn Gln Phe Ser Ser Gly Glu Lys Asn
    50                  55                  60
Ile Phe Leu Ala Ser Phe Val His Glu Tyr Ser Arg Arg His Pro Gln
65                  70                  75                  80
Leu Ala Val Ser Val Ile Leu Arg Val Ala Lys Gly Tyr Gln Glu Leu
                85                  90                  95
Leu Glu Lys Cys Phe Gln Thr Glu Asn Pro Leu Glu Cys Gln Asp Lys
                100                 105                 110
Gly Glu Glu Glu Leu Gln Lys Tyr Ile Gln Glu Ser Gln Ala Leu Ala
            115                 120                 125
Lys Arg Ser Cys Gly Leu Phe Gln Lys Leu Gly Glu Tyr Tyr Leu Gln
    130                 135                 140
Asn Glu Phe Leu Val Ala Tyr Thr Lys Lys Ala Pro Gln Leu Thr Ser
145                 150                 155                 160
Ser Glu Leu Met Ala Ile Thr Arg Lys Met Ala Ala Thr Ala Ala Thr
                165                 170                 175
Cys Cys Gln Leu Ser Glu Asp Lys Leu Leu Ala Cys Gly Glu Gly Ala
                180                 185                 190
```

```
Ala Asp Ile Ile Ile Gly His Leu Cys Ile Arg His Glu Met Thr Pro
        195                 200                 205
Val Asn Pro Gly Val Gly Gln Cys Cys Thr Ser Ser Tyr Ala Asn Arg
        210                 215                 220
Arg Pro Cys Phe Ser Ser Leu Val Val Asp Glu Thr Tyr Val Pro Pro
225                 230                 235                 240
Ala Phe Ser Asp Asp Lys Phe Ile Phe His Lys Asp Leu Cys Gln Ala
                245                 250                 255
Gln Gly Val Ala Leu Gln Arg Met Lys Gln Gly Phe Leu Ile Asn Leu
            260                 265                 270
Val Lys Gln Lys Pro Gln Ile Thr Glu Glu Gln Leu Glu Ala Leu Ile
        275                 280                 285
Ala Asp Phe Ser Gly Leu Leu Glu Lys Cys Cys Gln Gly Gln Glu Gln
        290                 295                 300
Glu Val Cys Phe Ala Glu Glu Gly Gln Lys Leu Ile Ser Lys Thr Gly
305                 310                 315                 320
Ala Ala Leu Gly Val
                325

<210> SEQ ID NO 9
<211> LENGTH: 30
<212> TYPE: DNA
<213> ORGANISM: Homo sapiens

<400> SEQUENCE: 9
aaaaaaggta ccacactgca tagaaatgaa                                              30

<210> SEQ ID NO 10
<211> LENGTH: 33
<212> TYPE: DNA
<213> ORGANISM: Homo sapiens

<400> SEQUENCE: 10
aaaaaaggat ccttagcttt ctcttaattc ttt                                          33

<210> SEQ ID NO 11
<211> LENGTH: 33
<212> TYPE: DNA
<213> ORGANISM: Homo sapiens

<400> SEQUENCE: 11
aaaaaaatcg atatgagctt gttaaatcaa cat                                          33

<210> SEQ ID NO 12
<211> LENGTH: 33
<212> TYPE: DNA
<213> ORGANISM: Homo sapiens

<400> SEQUENCE: 12
aaaaaaggat ccttagctct cctggatgta ttt                                          33

<210> SEQ ID NO 13
<211> LENGTH: 33
<212> TYPE: DNA
<213> ORGANISM: Homo sapiens

<400> SEQUENCE: 13
aaaaaaatcg atatgcaagc attggcaaag cga                                          33
```

```
<210> SEQ ID NO 14
<211> LENGTH: 33
<212> TYPE: DNA
<213> ORGANISM: Homo sapiens

<400> SEQUENCE: 14
aaaaaaggat ccttaaactc ccaaagcagc acg                                33

<210> SEQ ID NO 15
<211> LENGTH: 33
<212> TYPE: DNA
<213> ORGANISM: Homo sapiens

<400> SEQUENCE: 15
aaaaaaatcg atatgtccta catatgttct caa                                33

<210> SEQ ID NO 16
<211> LENGTH: 9
<212> TYPE: PRT
<213> ORGANISM: Homo sapiens

<400> SEQUENCE: 16

Ser Tyr Ile Cys Ser Gln Gln Asp Thr
1               5
```

RECOMBINANT HUMAN ALPHA-FETOPROTEIN AS AN IMMUNOSUPPRESSIVE AGENT

This application is a continuation of, and claims priority from, U.S. application Ser. No. 08/377,309, filed Jan. 24, 1995, U.S. Pat. No. 5,965,528.

BACKGROUND OF THE INVENTION

This invention relates to methods for treating autoimmune diseases.

Responses of the immune system initiate the destruction and elimination of invading organisms and toxic molecules produced by them. Because these immune reactions are destructive, it is essential that they be made in response only to molecules that are foreign to the host and not to those of the host itself. The ability to distinguish foreign molecules from self molecules is a fundamental feature of the immune system. Occasionally the immune system fails to make this distinction and reacts destructively against the host's own molecules; such autoimmune diseases can be fatal. Thus, tolerance to self antigens breaks down, causing the components of the immune system such as T or B cells (or both) to react against their own tissue antigens. Multiple sclerosis, rheumatoid arthritis, myasthenia gravis, insulin-dependent diabetes mellitus, and systemic lupus erythematosus are a few examples of such autoimmune diseases.

SUMMARY OF THE INVENTION

I have discovered that unglycosylated recombinant human alpha-fetoprotein made in a prokaryote (e.g., *E. coli*) is useful for inhibiting autoreactive immune cells derived from a mammal. Accordingly, the invention features a method of inhibiting autoreactive immune cell proliferation in a mammal (e.g., a human patient), involving administering to the mammal a therapeutically effective amount of recombinant human alpha-fetoprotein or an immune cell anti-proliferative fragment or analog thereof. Preferably, such immune cells include T cells or B cells; and the recombinant human alpha-fetoprotein used in such methods is produced in a prokaryotic cell (e.g., *E. coli*) and is unglycosylated.

In another aspect, the invention features a method of treating an autoimmune disease in a mammal (e.g., a human patient), involving administering to the mammal a therapeutically effective amount of recombinant human alpha-fetoprotein or an immune cell anti-proliferative fragment or analog thereof. Such an autoimmune disease is multiple sclerosis; is rheumatoid arthritis; is myasthenia gravis; is insulin-dependent diabetes mellitus; or is systemic lupus erythematosus. In yet other preferred embodiments the autoimmune disease is acquired immune deficiency syndrome or is a rejection of a transplanted organ, tissue or cell. Preferably, the recombinant human alpha-fetoprotein used in such methods is produced in a prokaryotic cell (e.g., *E. coli*) and is unglycosylated. In other preferred embodiments, such methods further involve administering to the mammal an immunosuppressive agent in an effective dose which is lower than the standard dose when the immunosuppressive agent is used by itself. Preferably, such an immunosuppressive agent is cyclosporine; is a steroid; is azathioprine; is FK-506; or is 15-deoxyspergualin. In yet another preferred embodiment, such a method involves administering to the mammal a tolerizing agent. Preferably, the recombinant human alpha-fetoprotein used in such methods is produced in a prokaryotic cell (e.g., *E. coli*) and is unglycosylated.

By "immune cell anti-proliferative" is meant capable of inhibiting the growth of an undesirable immune cell e.g., an autoreactive T cell as measured using the assays described herein).

By "therapeutically effective amount" is meant a dose of unglycosylated recombinant human alpha-fetoprotein (or a fragment or analog thereof) capable of inhibiting autoreactive immune cell proliferation.

By "recombinant human alpha-fetoprotein" is meant a polypeptide having substantially the same amino acid sequence as the protein encoded by the human alpha-fetoprotein gene as described by Morinaga et al., *Proc. Natl. Acad. Sci., USA* 80: 4604 (1983). The method of producing recombinant human alpha-fetoprotein in a prokaryotic cell is described in U.S. Ser. No. 08/133,773 issuing as U.S. Pat. No. 5,384,250.

According to the invention, administration of recombinant human alpha-fetoprotein ("rHuAFP") (or a fragment or analog thereof) can be an effective means of preventing or treating or ameliorating autoimmune diseases in a mammal. To illustrate this, I have shown that recombinant HuAFP produced in a prokaryotic expression system is effective in suppressing T cell proliferation in response to self antigens, despite the fact that such rHuAFP is not modified in the same fashion as naturally occurring HuAFP. The use of natural HuAFP has heretofore been limited by its unavailability, natural HuAFP is obtained by laborious purification from limited supplies of umbilical cords and umbilical cord serum. Because biologically rHuAPP can now be prepared in large quantities using the techniques of recombinant DNA, the use of rHuAFP for treating autoimmune diseases is now possible. The use of rHuAFP is especially advantageous since there are no known adverse side effects related to human alpha-fetoprotein and it is believed that relatively high doses can be safely administered.

Other features ahd advantages of the invention will be apparent from the following detailed description, and from the claims.

DETAILED DESCRIPTION

The drawings will first be described.

Drawings

FIG. 1 is a series of panels (FIGS. 1A–1D) showing the purity and biochemical characteristics of rHuAFP using polyacrylamide gel electrophoresis and column chromatography. FIGS. 1A is a 10% non-denaturing alkaline polyacrylamide gel showing the purity of rHuAFP produced in *E. coli*. Mouse amniotic fluid proteins (transferrin, AFP and albumin) are shown in lane 1, natural HuAFP and rHuAFP are shown in lane 2 and lane 3, respectively. FIG. 1B is a 10% sodium dodecyl sulfate-polyacrylamide gel showing the purity of rHuAFP produced in *E. coli*. Molecular weight markers are shown in lane 1, natural HuAFP and rHuAFP are shown in lane 2 and lane 3, respectively. FIG. 1C is a series of FPLC chromatograms of natural HuAFP and rHuAFP eluted on a MonoQ anion exchange column. The superimposed chromatograms identify natural HuAFP (Chromatogram 1) and rHuAFP (Chromatogram 2). FIG. 1D is a series of HPLC chromatograms obtained by passing 50 μg of natural and rHuAFP by passing through a reverse phase Delta Pak C18 column (Waters) and eluting with a gradient of 0–100% acetonitrile in 0.1% TFA. The superimposed chromatograms identify natural HuAFP (Chromatogram 1) and rHuAFP (Chromatogram 2).

FIG. 2 is a series of graphs showing the inhibitory effects of the rHuAFP on kinetics of T cell activation (FIG. 2A) and the dose-response relationship of rHuAFP on autoproliferating T cells (FIG. 2B). FIG. 2A is a graph showing proliferative responses over a 4 day time course of cells cultured in the absence (▽) and in the presence of 100 μg/ml (▲) rHuAFP. (●) denotes the background proliferation of the responder cell population cultured separately. Recombinant HuAFP-mediated suppression on the AMLR over the time course was significant ($p<0.01$). FIG. 2B is a graph showing the inhibition of autoproliferating T cells at 144 hours with amounts of rHuAFP ranging from 6–100 μg/ml (▲). (▽) denotes the control response of the reaction in the absence of protein. Inhibition of autoreactive T cells by rHuAFP in the range of 12.5–100 μg/ml is significant ($p<0.005$).

FIG. 4 is the nucleotide sequence (SEQ ID NO: 1) and deduced amino acid sequence (SEQ ID NO: 2) of the cDNA encoding human alpha-fetoprotein.

PRODUCTION OF RECOMBINANT HUMAN ALPHA-FETOPROTEIN

Figure 1A:
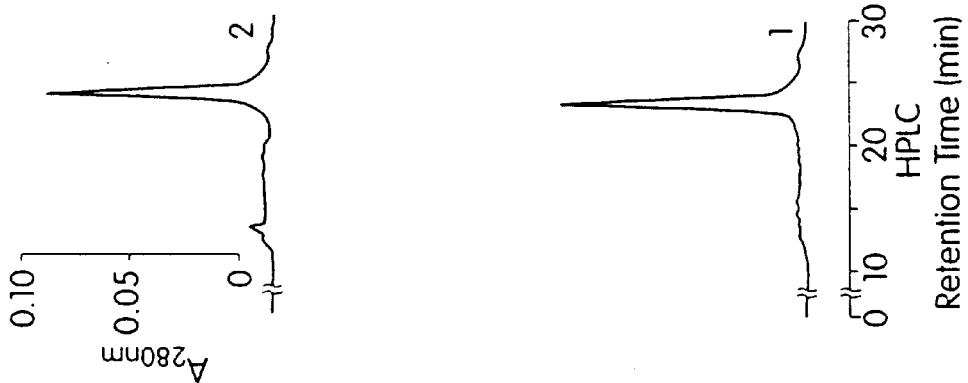

As summarized above, the invention includes therapies for the prevention and treatment of autoimmune diseases involving recombinant human alpha-fetoprotein ("rHuAFP") or fragments or analogs thereof. Methods for producing such rHuAFP in a prokaryotic cell are described in U.S. Ser. No. 08/133,773 and in U.S. Pat. No. 5,384,250, issued Jan. 24, 1995.

Fragments and Analogs

The invention includes biologically active fragments of rHuAFP. A biologically active fragment of rHuAFP is one that possesses at least one of the following activities: (a) directs a specific interaction with a target cell, e.g., binds to a cell expressing a receptor which is recognized by rHuAFP (e.g., the membrane of an autoreactive immune cell); or (b) halts, reduces, or inhibits the growth of an autoreactive immune cell (e.g., binds to a cell surface receptor and imparts an anti-proliferative signal); or (c) blocks, inhibits, or prevents an immunopathologic antibody reaction. The ability of rHuAFP fragments or analogs to bind to a receptor which is recognized by rHuAFP can be tested using any standard binding assay known in the art. Methods for assaying the biological activity or rHuAFP fragments and analogs are also known in the art, e.g., those described herein. Accordingly, a rHuAFP fragment, like the full-length rHuAFP molecule, can be used inhibit autoreactive immune cell proliferation.

In general, fragments of rHuAFP are produced according to the techniques of polypeptide expression and purification described in U.S. Ser. No. 08/133,773 (U.S. Pat. No. 5,384,250). For example, suitable fragments of rHuAFP can be produced by transformation of a suitable host bacterial cell with part of an HuAFP-encoding cDNA fragment (e.g., the cDNA described above) in a suitable expression vehicle. Alternatively, such fragments can be generated by standard techniques of PCR and cloned into the expression vectors (supra). Accordingly, once a fragment of rHuAFP is expressed, it may be isolated by various chromatographic and/or immunological methods known in the art. Lysis and fractionation of rHuAFP-containing cells prior to affinity chromatography may be performed by standard methods. Once isolated, the recombinant protein can, if desired, be further purified, e.g., by high performance liquid chromatography (see, e.g., Fisher, *Laboratory Techniques In Biochemistry And Molecular Biology*, Work and Burdon, eds., Elsevier, 1980).

A rHuAFP fragment may also be expressed as a fusion protein with maltose binding protein produced in *E. coli*. Using the maltose binding protein fusion and purification system (New England Biolabs), the cloned human cDNA sequence can be inserted downstream and in frame of the gene encoding maltose binding protein (malE), and the malE fusion protein can then be overexpressed. In the absence of convenient restriction sites in the human cDNA sequence, PCR can be used to introduce restriction sites compatible with the vector at the 5' and 3' end of the cDNA fragment to facilitate insertion of the cDNA fragment into the vector.

Following expression of the fusion protein, it can be purified by affinity chromatography. For example, the fusion protein can be purified by virtue of the ability of the maltose binding protein portion of the fusion protein to bind to amylose immobilized on a column.

To facilitate protein purification, the pMalE plasmid contains a factor Xa cleavage site upstream of the site into which the cDNA is inserted into the vector. Thus, the fusion protein purified as described above can then be cleaved with factor Xa to separate the maltose binding protein from a fragment of the recombinant human cDNA gene product. The cleavage products can be subjected to further chromatography to purify rHuAFP from the maltose binding protein. Alternatively, a fragment of rHuAFP may be expressed as a fusion protein containing a polyhistidine tag can be produced. Such an alpha-fetoprotein fusion protein may then be isolated by binding of the polyhistidine tag to an affinity column having a nickel moiety which binds the polyhistidine region with high affinity. The fusion protein may then be eluted by shifting the pH within the affinity column. The rHuAFP can be released from the polyhistidine sequences present in the resultant fusion protein by cleavage of the fusion protein with specific proteases.

Recombinant HuAFP fragment expression products (e.g., produced by any of the prokaryotic systems described in U.S. Ser. No. 08/133,773) may be assayed by immunological procedures, such as Western blot, immunoprecipitation analysis of recombinant cell extracts, or immunofluorescence (using, e.g., the methods described in Ausubel et al., *Current Protocols In Molecular Biology*, Greene Publishing Associates and Wiley Interscience (John Wiley & Sons), New York, 1994).

Once a fragment of rHuAFP is expressed, it is isolated using the methods described supra. Once isolated, the fragment of rHuAFP can, if desired, be further purified by using the techniques described supra. Fragments can also be produced by chemical synthesis (e.g., by the methods described in *Solid Phase Peptide Synthesis*, 2nd ed., 1984, The Pierce Chemical Co., Rockford, Ill.). The ability of a candidate rHuAFP fragment to exhibit a biological activity of alpha-fetoprotein is assessed by methods known to those skilled in the art (e.g., those described herein).

The purified recombinant gene product or fragment thereof can then be used to raise polyclonal or monoclonal antibodies against the human recombinant alpha-fetoprotein using well-known methods (see Coligan et al., eds., *Current Protocols in Immunology*, 1992, Greene Publishing Associates and Wiley-Interscience). To generate monoclonal antibodies, a mouse can be immunized with the recombinant protein, and antibody-secreting B cells isolated and immortalized with a non-secretory myeloma cell fusion partner. Hybridomas are then screened for production of recombinant human alpha-fetoprotein (or a fragment or analog thereof)-specific antibodies and cloned to obtain a homogenous cell population which produces monoclonal antibodies.

As used herein, the term "fragment," as applied to a rHuAFP polypeptide, is preferably at least 20 contiguous amino acids, preferably at least 50 contiguous amino acids, more preferably at least 100 contiguous amino acids, and most preferably at least 200 to 400 or more contiguous amino acids in length. Fragments of rHuAFP molecules can be generated by methods known to those skilled in the art, e.g., proteolytic cleavage or expression of recombinant peptides, or may result from normal protein processing (e.g., removal of amino acids from nascent polypeptide that are not required for biological activity).

Recombinant HuAFP fragments of interest include, but are not limited to, Domain I (amino acids 1 (Thr)-197 (Ser), see FIG. 4, SEQ ID NO: 3), Domain II (amino acids 198 (Ser)-389 (Ser), see FIG. 4, SEQ ID NO: 4), Domain III (amino acids 390 (Gln)-590 (Val), see FIG. 4, SEQ ID NO: 5), Domain I+II (amino acids 1 (Thr)-389 (Ser), see FIG. 4, SEQ ID NO: 6), Domain II+III (amino acids 198 (Ser)-590 (Val), see FIG. 4, SEQ ID NO: 7), and rHuAFP Fragment I (amino acids 266 (Met)-590 (Val), see FIG. 4, SEQ ID NO: 8). Activity of a fragment is evaluated experimentally using conventional techniques and assays, e.g., the assays described herein.

The invention further includes analogs of full-length rHuAFP or fragments thereof. Analogs can differ from rHuAFP by amino acid sequence differences, or by modifications (e.g., post-translational modifications) which do not affect sequence, or by both. Analogs of the invention will generally exhibit at least 80%, more preferably 85%, and most preferably 90% or even 99% amino acid identity with all or part of a rHuAFP amino acid sequence. Modifications (which do not normally alter primary sequence) include in vivo, or in vitro chemical derivatization of polypeptides, e.g., acetylation, or carboxylation; such modifications may occur during polypeptide synthesis or processing or following treatment with isolated modifying enzymes. Analogs can also differ from the naturally occurring rHuAFP by alterations in primary sequence, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity. These include genetic variants, both natural and induced (for example, resulting from random mutagenesis by irradiation or exposure to ethanemethylsulfate or by site-specific mutagenesis as described in Sambrook et al., *Molecular Cloning: A Laboratory Manual*, 2nd ed., Cold Spring Harbor Press, 1989, or Ausubel et al., supra)). Also included are cyclized peptide molecules and analogs which contain residues other than L-amino acids, e.g., D-amino acids or non-naturally occurring or synthetic amino acids, e.g., β or γ amino acids, or L-amino acids with non-natural side chains (see e.g., Noren et al., *Science* 244:182, 1989).

Methods for site-specific incorporation of non-natural amino acids into the protein backbone of proteins is described, e.g., in Ellman et al., *Science* 255:197, 1992. Also included are chemically synthesized polypeptides or peptides with modified peptide bonds (e.g., non-peptide bonds as described in U.S. Pat. No. 4,897,445 and U.S. Pat. No. 5,059,653) or modified side chains to obtain the desired pharmaceutical properties as described herein. Useful mutants and analogs are identified using conventional methods, e.g., those described herein.

The cloning, expression, isolation and characterization of exemplary rHuAFP fragments now follows. These examples are provided to illustrate, not limit, the invention.

EXPERIMENTAL

MATERIALS AND METHODS

Polymerase Chain Reaction (PCR) rHuAFP Fraqments

Plasmid constructs encoding fragments of human alpha-fetoprotein were prepared using polymerase chain reaction (PCR) techniques known to those skilled in the art of molecular biology, using oligonucleotide primers designed to amplify specific portions of the human alpha-fetoprotein gene (see e.g., PCR Technology, H. A. Erlich, ed., Stockton Press, New York, 1989; *PCR Protocols: A Guide to Methods and Applications*, M. A. Innis, David H. Gelfand, John J. Sninsky, and Thomas J. White, eds., Academic Press, Inc., New York, 1990, and Ausubel et. al., supra).

The following six rHuAFP fragments were prepared to evaluate their biological activity (e.g., according to the methods disclosed herein):

| | | |
|---|---|---|
| Domain I | Amino acids 1 (Thr)–197 (Ser), | (FIG. 4, SEQ ID NO:3) |
| Domain II | Amino acids 198 (Ser)–389 (Ser), | (FIG. 4, SEQ ID NO:4) |
| Domain III | Amino acids 390 (Gln)–590 (Val), | (FIG. 4, SEQ ID NO:5) |
| Domain I + II | Amino acids 1 (Thr)–389 (Ser), | (FIG. 4, SEQ ID NO:6) |
| Domain II + III | Amino acids 198 (Ser)–590 (Val), | (FIG. 4, SEQ ID NO:7) |
| rHuAFP Fragment I | Amino acids 266 (Met)–590 (Val), | (FIG. 4, SEQ ID NO:8) |

Amino acid sequences were deduced from those for human alpha-fetoprotein (1 (Thr)-590 (Val); SEQ ID NO: 2) shown in FIG. 4. Fragments of rHuAFP designated Domain I, Domain II, Domain III, Domain I+II, Domain II+III and rHuAFP Fragment I were synthesized using standard PCR reaction conditions in 100 μL reactions containing 34 μL H$_2$O, 10 μL 1X reaction buffer, 20 μL 1 mM dNTP, 2 μL DNA template (HuAFP cloned in pI18), appropriate 5' and 3' oligonucleotide primers (10 μL 10 pmol/μL 5' primer, 10 μL 10 pmol/μL 3' primer), 1 μL glycerol, 10 μL DMSO, and 1 μL Pfu polymerase (Stratagene, LaJolla, Calif.). Primers used for PCR amplifications were:

| | | |
|---|---|---|
| DomI25 | 5'-AAAAAAGGTACCACACTGCATAGAAATGAA-3' | (SEQ ID NO:9) |
| DomI3 | 5'-AAAAAAGGATCCTTAGCTTTCTCTTAATTCTTT-3' | (SEQ ID NO:10) |
| DomII5 | 5'-AAAAAAATCGATATGAGCTTGTTAAATCAACAT-3' | (SEQ ID NO:11) |

-continued

| | | |
|---|---|---|
| DomII3 | 5'-AAAAAAGGATCCTTAGCTCTCCTGGATGTATTT-3' | (SEQ ID NO:12) |
| DomIII5 | 5'-AAAAAAATCGATATGCAAGCATTGGCAAAGCGA-3' | (SEQ ID NO:13) |
| DomIII3 | 5'-AAAAAAGGATCCTTAAACTCCCAAAGCAGCACG-3' | (SEQ ID NO:14) |
| 5'rHuAFP Fragment I | 5'-AAAAAAATCGATATGTCCTACATATGTTCTCAA-3' | (SEQ ID NO:15) |

Accordingly, primer pairs DomI25 and DomI3, DomII5 and DomII3, DomIII5 and DomIII3, 5'rHuAFP Fragment I and DomIII3, DomI25 and DomII3, and DomII5 and DomIII3 were used to isolate cDNA sequences of Domain I, Domain II, Domain III, rHuAFP Fragment I, Domain I+II, and Domain II+III, respectively, of rHuAFP. Annealing, extension, and denaturation temperatures were 50° C., 72° C., and 94° C., respectively, for 30 cycles. PCR products were purified according to standard methods. Purified PCR products encoding Domain I and Domain I+II were digested individually with KpnI and BamHI and cloned separately into KpnI/BamHI-treated pTrp4. Purified PCR products encoding Domain II, Domain III, Domain II+III, and rHuAFP Fragment I were digested individually with Bsp106I and BamHI and were cloned separately into Bsp106I/BamHI-treated pTrp4. Each plasmid construct was subsequently transformed into competent E. coli cells. Since the expression product will begin with the amino acid sequence encoded by the translation start signal methionine, it is expected that such signal will be removed, or in any event, not affect the bioactivity of the ultimate expression product.

Autologous Mixed Lymphocyte Reactions (AMLR)

AMLR assays were performed as described below.

RESULTS

Expression and Purification

Figure 5:
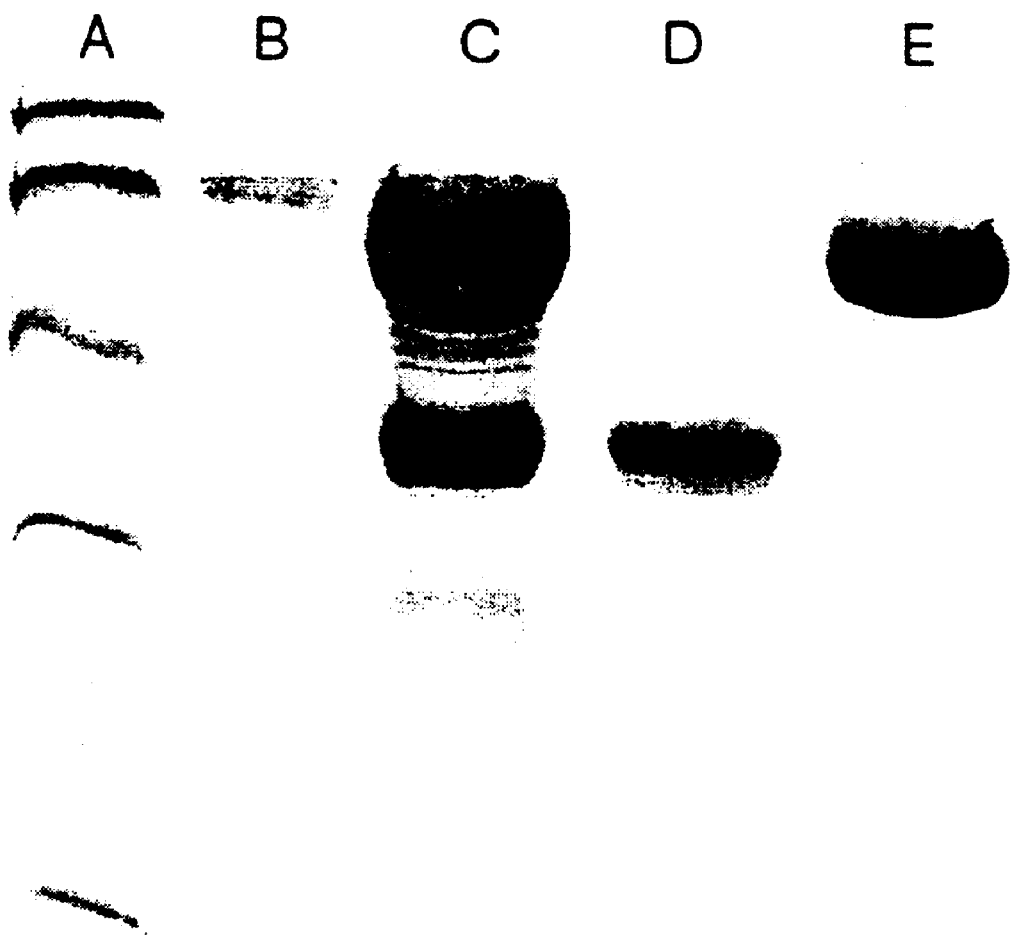
FIG. 5 is the 10% SDS-PAGE analysis of rHuAFP Fragment I or alpha-fetoprotein (Lane A, MW marker; Lane B, natural human alpha-fetoprotein, Lane C, unpurified rHuAFP and rHuAFP Fragment I, Lane D, purified rHuAFP Fragment I, and Lane E, purified full-length rHuAFP).

E. coli containing the expression plasmid encoding rHuAFP Fragment I was cultured and purified. FIG. 5 (lane D) shows the SDS-PAGE profile of the purified rHuAFP Fragment I. N-terminal amino acid sequence analysis showed that rHuAFP Fragment I possessed the amino acid sequence $Ser_{267}$-Tyr-Ile-Cys-Ser-Gln-Gln-Asp-$Thr_{275}$ (SEQ ID NO: 16) which corresponds to the expected N-terminal amino acid sequence of rHuAFP Fragment I (see FIG. 4, SEQ ID NO: 2) where the initiating methionine is cleaved intracellularly.

Inhibition of the Autologous Mixed Lymphocyte Reactions (AMLR)

The immunosuppressive activity of 100 µg/ml rHuAFP Fragment I was assessed by its ability to suppress human autologous mixed lymphocyte reactions (AMLR). As shown in Table I, rHuAFP Fragment I inhibited the proliferative response of autoreactive lymphocytes stimulated by autologous non-T cells at 144 hours.

TABLE I

| Reaction Setup | Thymidine Incorporation (CPM) |
|---|---|
| T Cells | 7118 ± 964 |
| AMLR | 83103 ± 6480 |
| AMLR + rHuAFP Fragment I (100 µg/ml) | 29692 ± 2963 |

Recombinant HuAFP As An Immunosuppressive Agent

Immunosuppressive attributes of rHuAFP (or a fragment or analog thereof) is evaluated by any standard assay for analysis of immunoregulatory activity in vivo or in vitro. As discussed infra, the art provides a number of animal systems for in vivo testing of immunosuppressive characteristics of rHuAFP (or a fragment or analog thereof) on an autoimmune disease, e.g., the nonobese diabetic (NOD) mouse. Furthermore, a wide variety of in vitro systems are also available for testing immunosuppressive aspects of rHuAFP e.g., one such in vitro assay evaluates the inhibition of autoantigen-induced proliferation of T cells in an autologous mixed lymphocyte reaction (AMLR).

The following examples demonstrate that unglycosylated rHuAFP inhibits T cell autoproliferation in response to self antigens. These examples are provided to illustrate, not limit, the invention.

EXPERIMENTAL

MATERIALS AND METHODS

Gel Electrophoresis, Immunoblotting and Purification

The purity and characterization of rHuAFP was evaluated by sodium dodecyl sulfate-polyacrylamide gel electrophoresis (SDS-PAGE) and nondenaturing alkaline PAGE (APAGE) according to standard methods. Gels were subsequently analyzed either by staining with Coomassie brilliant blue or by transferring electrophoretically separated polypeptides to Immobilon PVDF membranes (Millipore, Mississauga, ON) for immunoblotting analysis. Recombinant HuAFP-monospecific rabbit anti-natural HuAFP polyclonal antibody complexes were identified by alkaline-phosphatase-conjugated goat anti-rabbit IgG and the immunoreactive bands were detected with the BCIP/NBT color development solution (Bio-Rad-Laboratories, Mississauga, ON) according to the manufacturer's instructions.

Column chromatography was performed according to standard methods.

Autologous Mixed Lymphocyte Reactions (AMLR)

Isolation of human peripheral blood mononuclear cells (PBMC), their fractionation into non-T cell populations, and the AMLR, were performed according to standard procedures. Responder T cells were isolated by passing $1.5 \times 10^8$ PMBC over a commercial Ig-anti-Ig affinity column (Biotek Laboratories) and $2 \times 10^5$ responder cells were subsequently cultured with $2 \times 10^5$ autologous $^{137}$Cs-irradiated (2500 rads) non-T stimulator cells from a single donor. The medium employed consisted of RPMI-1640 supplemented with 20 mM HEPES (Gibco), $5 \times 10^{-5}$ M 2-mercaptoethanol (BDH, Montreal, QC), 4 mM L-glutamine (Gibco), 100 U/ml penicillin (Gibco) and 100 µg/ml streptomycin sulfate, with the addition of 10% fresh human serum autologous to the responder T cell donor for the AMLR. Varying concentrations of purified rHuAFP, human serum albumin (HSA), anti-HuAFP monoclonal antibodies clone #164 (125 µg/ml final concentration in culture) (Leinco Technologies, St. Louis, Mo.) were added at the initiation of cultures. AMLR cultures were incubated for 4 to 7 days, at 37° C. in 95% air and 5% $CO_2$. At the indicated intervals, DNA synthesis was assayed by a 6 hour pulse with 1 µCi of $^3$H-thymidine (specific activity 56 to 80 Ci/mmole, ICN). The cultures were harvested on a multiple sample harvester (Skatron, Sterling, Va.), and the incorporation of $^3$H-TdR was measured in a Packard 2500 TR liquid scintillation counter. Results are expressed as mean cpm±the standard error of the mean of triplicate or quadruplicate cultures.

RESULTS

Expression and Purification

Figure 1B:
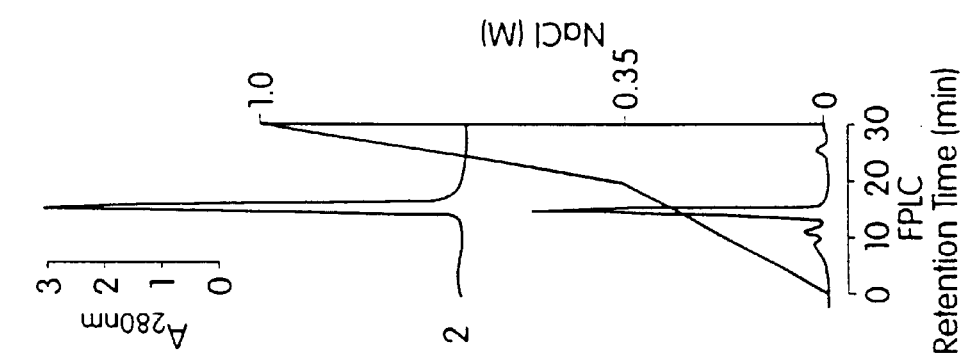
Figure 1C:
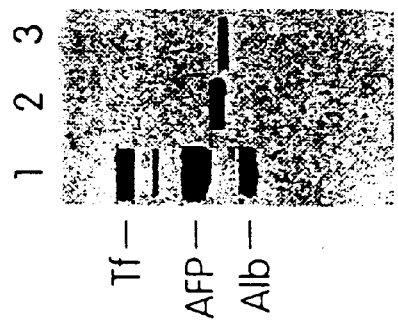
Figure 1D:
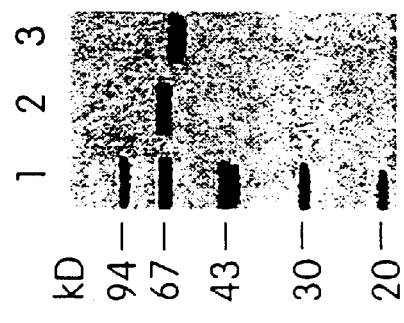

Purity of isolated rHuAFP expressed in E. coli was verified as a single band on Coomassie stained APAGE and SDS-PAGE are shown in FIGS. 1A–1B, respectively. Soluble monomeric rHuAFP derived from E. coli was obtained by eluting a protein fraction containing rHuAFP employing Q-sepharose chromatography. Approximately 1 mg of pure rHuAFP per liter of bacterial culture was recovered as a single homogeneous peak by FPLC Mono-Q anion exchange with 220–230 mM NaCl and migrated at approximately 65 kD on SDS-PAGE (FIG. 1B). Recombinant HuAFP exhibits a lower molecular weight on SDS-PAGE than natural HuAFP, since prokaryotic expression systems lack the enzymatic machinery required for glycosylation of proteins. Rechromatographed samples of pure rHuAFP on FPLC and HPLC yielded a single peak as shown in FIG. 1C and FIG. 1D, confirming the purity of the rHuAFP preparation. In addition, N-terminal sequencing data correspond to the expected amino acid sequence at the N-terminus of rHuAFP.

Inhibition of the Autologous Mixed Lymphocyte Reactions (AMLR)

Figure 2A:
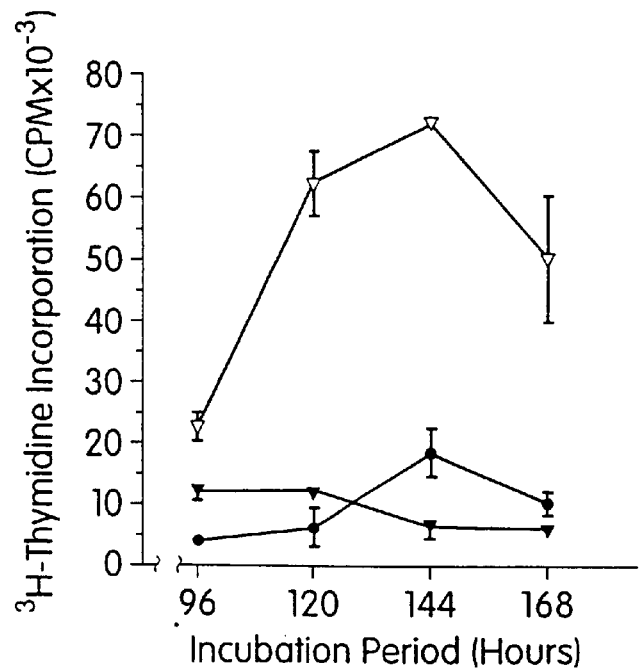
Figure 2B:
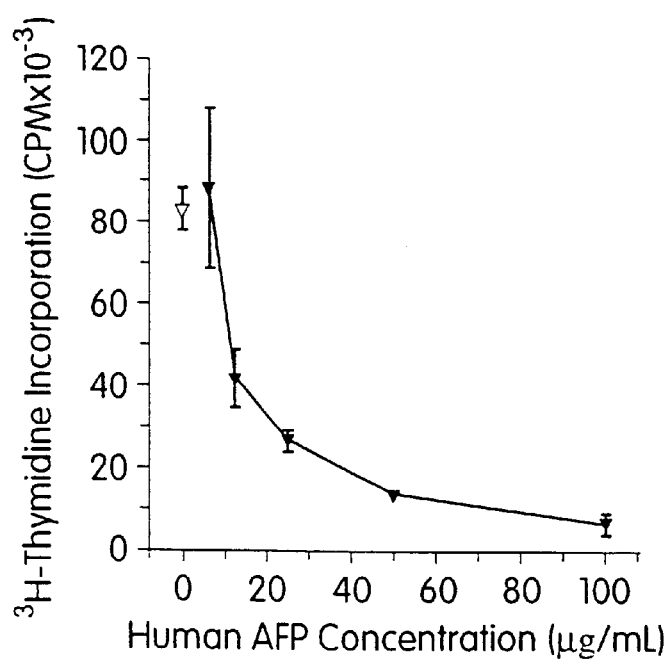

The immunosuppressive activity of rHuAFP was assessed by its ability to suppress human autologous mixed lymphocyte reactions (AMLR). As shown in FIG. 2A, rHuAFP inhibited the proliferative response of autoreactive lymphocytes stimulated by autologous non-T cells, throughout the 4 to 7 day time course measuring autoproliferation. Results from dose-response studies performed at the peak of T cell autoproliferation, as shown in FIG. 2B, demonstrate that the addition of rHuAFP at the initiation of cultures suppressed the AMLR in a dose-dependent manner. Furthermore, parallel viability-studies established that the inhibitory activity of rHuAFP on human autoreactive T cells was not due to non-specific cytotoxic effects.

Figure 3:
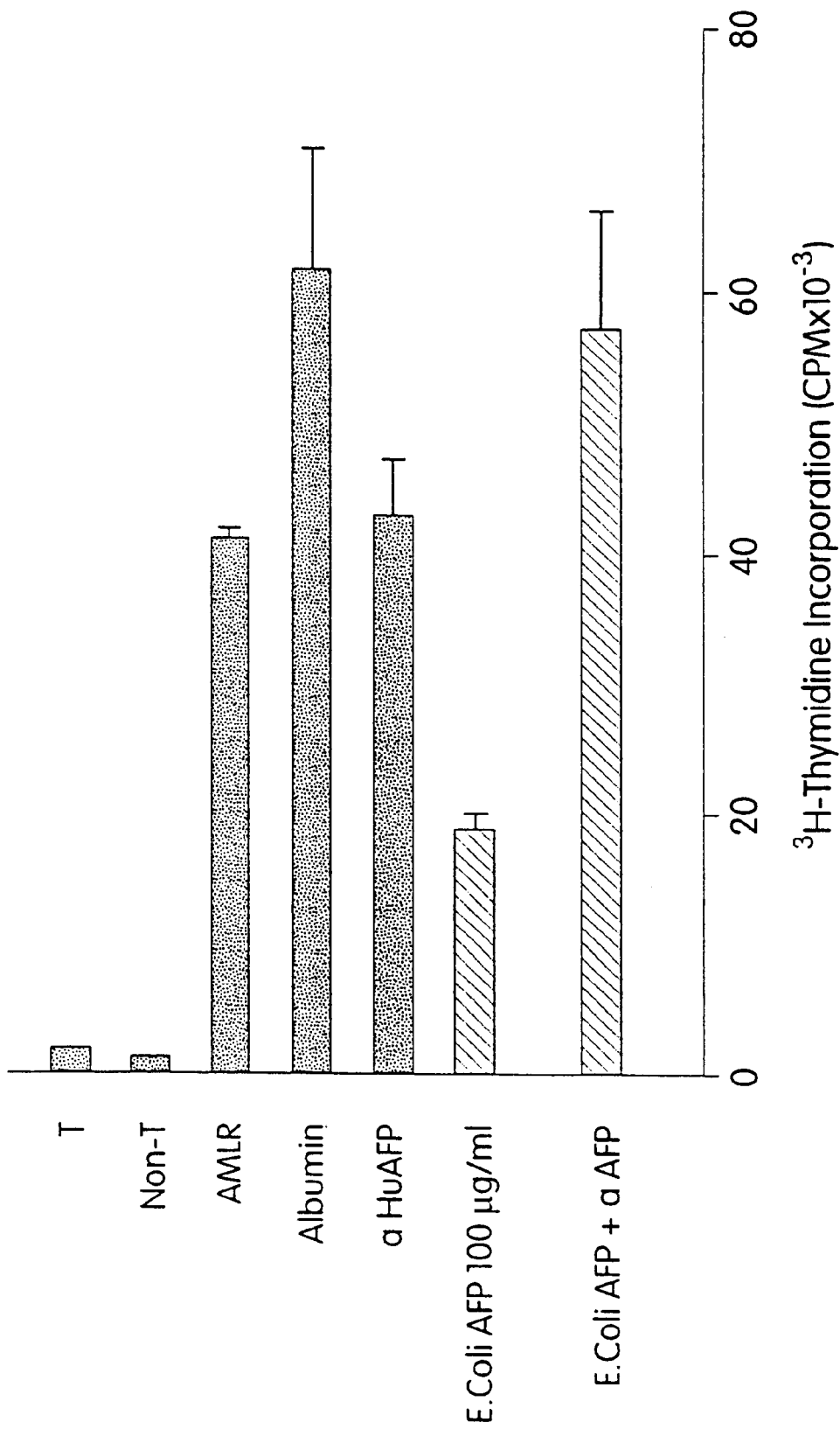
FIG. 3 is a bar graph showing that monoclonal anti-natural HuAFP antibodies block immunosuppression of the AMLR by rHuAFP. Immunosuppression by rHuAFP was significant ($p<0.002$) and blocking of rAFP-mediated immunosuppression by the AMLR by monoclonal anti-natural HuAFP antibodies was also significant ($p<0.03$).

To further substantiate that rHuAFP was the agent responsible for the inhibition of autoproliferating T cells, blocking of rHuAFP-mediated suppression of the AMLR was performed using commercial murine anti-human AFP monoclonal antibodies (MAb). As illustrated in FIG. 3, suppression of proliferating autoreactive T cells by 100 µg/ml of rHuAFP was completely blocked by anti-HuAFP NAb. The addition of 100 µg/ml of HSA did not diminish the AMLR response and the presence of MAb alone in the reaction culture was without any effect.

Recombinant polypeptides produced in prokaryotic expression systems are at risk for contamination with host cell lipopolysaccharide (LPS) during their isolation from bacteria. It has been demonstrated that small amounts of LPS can antagonize the biological activities of cytokines, thereby impairing the immune responsiveness of macrophages. Accordingly, the effect of endotoxin on various rHuAFP preparations was evaluated by performing AMLR experiments with recombinant protein depleted of endotoxin by passage over Detoxi-gel (Pierce) versus that of rHuAFP which was untreated. Results of these experiments showed that both preparations had equivalent levels of immunosuppressive activity.

As shown in FIG. 2A and FIG. 2B, the results of this study also demonstrate that rHuAFP suppresses the proliferation of autoreaction T cells with a potency equivalent to glycosylated nHuAFP by eliciting inhibitory effects on autoproliferating T cells throughout the in vitro reactions, with highly significant inhibition being achieved with rHuAFP concentrations ranging from 5 µg/ml to 100 µg/ml.

Autoimmune Disease

As is discussed above, autoimmune diseases are characterized by a loss of tolerance to self antigens, causing cells of the immune systems, e.g., T or B cells (or both), to react against self tissue antigens. Autoimmune diseases may involve any organ system, although some are affected more commonly than others. Examples of tissues affected by autoimmune conditions include: the white matter of the brain and spinal cord in multiple sclerosis; the lining of the joints in rheumatoid arthritis; and the insulin secreting β islet cells of the pancreas in insulin-dependent diabetes mellitus. Other forms of autoimmune disease destroy the connections between nerve and muscle in myasthenia gravis or destroy the kidneys and other organs-in systemic lupus erythematosus. Examples of other autoimmune diseases include, without limitation, Addison's disease, Crohn's disease, Graves' disease, psoriasis, scleroderma, and ulcerative colitis.

The art provides a wide variety of experimental animal systems, transgenic and non-transgenic, for testing therapies for human illness involving autoimmune diseases (see e.g., Paul, W. E., Fundamental Immunology, 2nd ed., Raven Press, New York, 1989; and Kandel et al. Principles of Neural Science, 3rd ed., Appleton and Lange, Norwalk, Conn., 1991; and Current Protocols In Immunology, Coligan, J. E., Kruisbeek, A. M., Margulies, D. H., Shevach, E. M., and Strober, eds., Green Publishing Associates (John Wiley & Sons), New York, 1992). Based on the above-described experimental results showing immunosuppressive activity of unglycosylated rHuAFP, it is reasonable to believe that other autoimmune diseases can be treated by administration of such rHuAFP (or fragment or analog thereof) produced in a prokaryotic system. Accordingly, the invention provides the use of rHuAFP (or a fragment or analog thereof) for treatment (i.e., prevention or suppression or amelioration or promotion of remission) of any autoimmune disease.

There now follow examples of animal systems useful for evaluating the efficacy of recombinant human alpha-fetoprotein or an immune cell anti-proliferative fragment or analog thereof in treating autoimmune diseases. These examples are provided for the purpose of illustrating, not limiting, the invention.

Multiple Sclerosis

Multiple sclerosis (MS) is a demyelinating disease involving scattered areas of the white matter of the central nervous system. In MS, myelin basic protein and proteolipid protein are the major targets of an autoimmune response involving T lymphocytes, among other immune system components. Loss of the myelin sheath of nerve cells (demyelination) occurs, resulting in neurological symptoms that culminate in coma or paralysis.

Experimental autoimmune encephalomyelitis (EAE) is a primary model used in the art to examine and assess the effectiveness of therapeutic agents for treating MS. EAE is an inflammatory autoimmune demyelinating disease induced in laboratory animals by immunization with central nervous system tissue. When animals (e.g., mice, rats, guinea pigs, rabbits, monkeys, etc.) are injected with adjuvant, e.g., complete Freund's adjuvant, plus myelin basic protein or proteolipid protein, EAE is induced, which is similar, pathologically to MS (see e.g., Alvord et al., *Experimental Allergic Encephalomyelitis-A Useful Model for Multiple Sclerosis*, Liss, New York, 1984; Swanborg, *Meth. Enzymol.* 162:413, 1988; and McCarron et al., *J. Immunol.*, 147: 3296, 1991.)

To evaluate rHuAFP or a fragment or analog thereof, EAE is induced in an appropriate laboratory animal, e.g., a mouse or rabbit, according to methods known in the art. To evaluate the compound's immunosuppressive effect on EAE, i.e., its ability to prevent or ameliorate EAE, the compound is administered according to standard methods, e.g., intravenously or intraperitoneal, at an appropriate dosage on a daily basis. Generally, administration is initiated prior to inducing EAE and/or after the clinical appearance of EAE. Control animals receive a placebo, e.g., human serum albumin, similarly administered as for rHuAFP or related molecules. The effect of the test molecules on EAE is monitored according to any standard method. For example, weight loss and muscle paralysis in EAE-induced animals is monitored on a daily basis. If desired, histological inspection (e.g., by using any standard histochemical or immunohistochemical procedure, see e.g., Ausubel et al., *Current Protocols In Molecular Biology*, Greene Publishing Associates (John Wiley & Son), New York, 1994; Bancroft and Stevens, *Theory and Practice of Histochemical Techniques*, Churchill Livingstone, 1982) of brain and spinal cord tissues is performed and tissue samples examined microscopically for evidence of EAE, e.g., evidence of perivascular cellular infiltrates. Comparative studies between treated and control animals are used to determine the relative efficacy of the test molecules in preventing or ameliorating EAE. A molecule which prevents or ameliorates (decreases or suppresses or relieves or promotes remission of) the symptoms of EAE is considered useful in the invention.

Rheumatoid Arthritis

Rheumatoid arthritis (RA) is a common chronic illness in which the synovial membrane of multiple joints becomes inflamed, causing damage to cartilage and bone. RA is associated with human lymphocyte antigen (HLA)-DR4 and considered to be an autoimmune disorder involving T cells, see e.g., Sewell et al., *Lancet* 341: 283, 1993. RA results from a complex interaction of synovial cells with various cellular elements (and their soluble products) that infiltrate from the circulation into the synovial lining of joints. A series of biological events occur which ultimately lead to a lesion which invades and erodes collagen and the cartilage matrix of the joint.

A number of animal models of RA, e.g., the MRL-lpr/lpr mouse, are known in the art which develop a form of arthritis resembling the human disease (see e.g., *Fundamental Immunology*, supra). Alternatively, autoimmune collagen arthritis (ACA) and adjuvant arthritis (AA) can be induced in an appropriate animal according to standard methods.

To evaluate rHuAFP or a fragment or analog thereof on immunosuppressive on RA, i.e., the compound's ability to prevent or ameliorate RA, the test molecule is administered to a MRL-lpr/lpr mouse according to standard methods, e.g., intravenously or intraperitoneally, at an appropriate dosage on a daily basis. Generally, administration is initiated prior to the onset of RA and/or after the clinical appearance of RA. Control animals receive a placebo, e.g., human serum albumin, similarly administered as for rHuAFP or related molecules. The effect of the test molecule on RA is monitored according to standard methods. For example, analysis of the cellular component(s) of a synovial joint are monitored on a daily basis. If desired, histological inspection (e.g., by using any standard histochemical or immunohistochemical procedure, see e.g., Ausubel et al., supra; Bancroft and Stevens, supra) of the synovial joint is performed and tissue samples examined microscopically for evidence of RA, e.g., evidence of erosion of collagen and cartilage matrix in a joint. Comparative studies between treated and control animals are used to determine the relative efficacy of the test molecule in preventing or ameliorating RA. A test molecule which prevents or ameliorates (decreases or suppresses or relieves or promotes remission of) the symptoms of RA is considered useful in the invention.

Myasthenia Gravis

Myasthenia gravis (MG) is a disorder of neuromuscular transmission in which there are autoantibodies against acetylcholine receptors of neuromuscular junctions. Antibodies attack the junction, causing weakness and paralysis. Females are afflicted twice as often as males, typically during the third decade of life. Muscular weakness is the predominant feature of the disease. Clinical signs include drooping of the eyelids and double vision. There is an association between MG and hyperthyroidism.

Experimental autoimmune MG (EAMG) has been studied in a variety of animals including rabbits, monkeys, Lewis rats and inbred strains of mice (see e.g., *Principles of Neural Science*, supra), the symptoms of EAMG resemble the essential characteristics of the human disease. A single injection of acetylcholine receptor, e.g., purified from the electric organs of the eel Torpedo californica, along with adjuvants, causes an acute phase of weakness within 8 to 12 days and then chronic weakness after about 30 days. The response to the eel receptor is T cell dependent. The C57BL/6 strain (H-2B) is a high responder to Torpedo receptor and highly susceptible to EAMG.

To evaluate rHuAFP or a fragment or analog thereof, EAMG is induced in an appropriate laboratory animal, e.g., the C57BL/6 strain (H-2B) mouse, according to methods known in the art. To evaluate the compound's immunosuppressive effect on EAMG, i.e., its ability to prevent or ameliorate EAMG, the compound is administered according to standard methods, e.g., intravenously or intraperitoneally, at an appropriate dosage on a daily basis. Generally, administration is initiated prior to inducing EAMG and/or after the clinical appearance of EAMG. Control animals receive a placebo, e.g., human serum albumin, similarly administered as for rHuAFP or related molecules. The effect of the test molecules on EAMG is monitored according to standard methods. For example, nerve stimulation in an electromyographic muscle assay (e.g., according to the methods of Pachner et al., *Ann. Neurol.* 11:48, 1982) in EAMG-induced animals can be assayed. If desired, histological inspection (e.g., by using any standard histochemical or immunohistochemical procedure, see e.g., Ausubel et al., supra; Bancroft and Stevens, supra) of tissue samples is performed and tissue samples examined microscopically for evidence of EAMG, e.g., evidence of monocyte infiltration and/or autoantibody localization at acetylcholine receptors of neuromuscular junctions. Comparative studies between treated and control animals are used to determine the relative efficacy of the test molecules in preventing or ameliorating EAMG. A molecule which prevents or ameliorates (decreases or suppresses or relieves or promotes remission of) the symptoms of EAMG is considered useful in the invention.

Insulin-Dependent Diabetes Mellitus

Diabetes is a disorder of glucose metabolism. Insulin-dependent diabetes mellitus (IDDM), also known as Type I diabetes, is an autoimmune disease characterized by T-cell mediated destruction of pancreatic β cells in the islets of Langerhans, accompanied by an immune response to a diversity of self peptides leading to hyperglycemia, among other pathological events. IDDM patients depend on exogenous insulin to maintain normal glucose metabolism. Humans at risk for developing IDDM can be identified prior to onset of hyperglycemia by the abnormal occurrence of autoantibodies to insulin, islet cells, glutamic acid carboxylase, as well as other autologous proteins (see e.g., Baekkeskov et al., *J. Clin. Invest.* 79:926, 1987; Dean et al., *Diabetologia* 29: 339, 1986; Rossini et al., *Annu. Rev. Immunol.* 3:289, 1985; Srikanta et al., *N. Enal. J. Med.* 308:322, 1983). Autoantibody patterns, in general, are predictive for the eventual disease progression and/or risk for developing the disease (see e.g., Keller et al., *Lancet* 341:927, 1993).

Examples of animal models which spontaneously develop IDDM resembling the human disease include the Bio-Breeding (BB) rat and nonobese diabetic (NOD) mouse. Diabetes is also experimentally induced by streptozotocin.

The BB rat spontaneously develops a disease similar to IDDM, with insulitis (infiltration of mononuclear cells into the pancreatic islets) and autoantibodies against self cells and insulin (see e.g., Baekkeskov et al., *J. Clin. Invest.* 79:926, 1987; Rossini et al, supra; Nakhooda et al., *Diabetes* 26: 100, 1977; Dean et al., *Clin. Exp. Immunol.* 69: 308, 1987).

NOD mice typically develop insulitis between 5 and 8 weeks of age, and by 7 months 70% of the females and 40% of the males become diabetic. T cells transferred from diabetic mice to young nondiabetic NOD mice induce diabetes within 2 to 3 weeks (see e.g., Bendelac et al., *J. Exp. Med.* 166:823, 1987). NOD mice usually die within 1 to 2 months after the onset of diabetes unless they receive insulin therapy.

Chemically induced diabetes is accomplished using multiple injections of small doses of streptozotocin, a drug toxic for pancreatic β cells, which causes severe insulitis and diabetes (see e.g., Kikutani et al., *Adv. Immunol.* 51:285, 1992).

Accordingly, the art provides a variety animal models resembling human IDDM which can be used to examine and assess approaches for the prevention or amelioration of diabetes involving rHuAFP (or a fragment or analog thereof).

To evaluate the immunosuppressive effect of rHuAFP or a fragment or analog thereof on the development of diabetes mouse, i.e., the compound's ability to treat or prevent insulitis and diabetes, the test compound is administered to an appropriate test animal, e.g, a NOD mouse, according to standard methods, e.g., intravenously or intraperitoneally, at an appropriate dosage on a daily basis. Generally, administration is initiated prior to the onset of insulitis and diabetes and/or after the clinical appearance of diabetic characteristics. control animals receive a placebo, e.g., human serum albumin, similarly administered as for rHuAFP or related molecules. The effect of test molecules on insulitis and diabetes is monitored according to standard methods. For example, weight loss, ketone body formation, and blood glucose concentration is monitored on a daily basis. If desired, histological inspection (e.g., by using any standard histochemical or immunohistochemical procedure, see e.g., Ausubel et al., supra; Bancroft and Stevens, supra) of pancreatic islet cells is performed and tissue samples examined microscopically for evidence of insulitis and β cell destruction. Comparative studies between treated and control animals are used to determine the relative efficacy of the test molecules in preventing or ameliorating the diabetic condition. A molecule which prevents or ameliorates (decreases or suppresses or relieves or promotes remission of) the symptoms of diabetes, e.g., IDDM, is considered useful in the invention.

Systemic LuPus Erythematosus

Systemic lupus erythematosus (SLE) is a severe systemic autoimmune disease. About 90% of patients with this disease are young women. This marked preponderance of females is not seen before puberty or after menopause. The illness generally begins in young adulthood when a characteristic skin rash appears over cheekbones and forehead. Hair loss is common, as is severe kidney damage, arthritis, accumulation of fluid around the heart and inflammation of the lining of the lungs. In nearly half of the patients the blood vessels of the brain also become inflamed, leading to paralysis and convulsions. The activity of the disease, like other autoimmune diseases, can fluctuate: long quiescent periods of good health can terminate abruptly and inexplicably with the onset of a new attack. A large number of different autoantibodies are known to occur in SLE, e.g., autoantibodies against DNA, RNA and histones (see, e.g., *Fundamental Immunology*, supra)

A number of animal models of human SLE, e.g., inbred mouse strains including NZB mice-and their $F_1$ hybrids, MRL mice, and BXSB mice, are known in the art (see e.g., Bielschowsky et al. *Proc. Univ. Otago Med. Sch.* 37:9, 1959; Braverman et al., *J. Invest. Derm.* 50: 483, 1968; Howie et al. *Adv. Immunol.* 9:215, 1968; *Genetic Control of Autoimmune Disease*, Rose, M., Bigazzi, P. E., and Warner, N. L. eds., Elsevier, Amsterdam, 1979; and *Current Protocols In Immunology*, supra). For example, the NZBXNZW $F_1$ mouse is an excellent model of human SLE, female mice develop high levels of anti-double- and single-stranded DNA autoantibodies, other anti-nuclear antibodies, and renal disease; death usually occurs at approximately 8 months (see e.g., Theofilopoulos et al., *Adv. Immunol.* 37:269, 1985).

To evaluate the immunosuppressive effect of rHuAFP or a fragment or analog thereof on SLE, i.e., the compound's ability of rHuAFP to prevent or ameliorate SLE, test compounds are administered to an appropriate animal, e.g., the NZBXNZW $F_1$ mouse, according to standard methods, e.g., intravenously or intraperitoneally, at an appropriate dosage on a daily basis. Generally, administration is initiated prior to the onset of SLE and/or after the clinical appearance of SLE. Control animals receive a placebo, e.g., human serum albumin, similarly administered as for rHuAFP or related molecules. The effect of the test compound on SLE is monitored according to standard methods. For example, analysis of autoantibodies, e.g., anti-DNA antibodies can be monitored. If desired, histological inspection (e.g., by using any standard histochemical or immunohistochemical procedure, see e.g., Ausubel et al., supra; Bancroft and Stevens, supra) of kidney tissue is performed and tissue samples examined microscopically for evidence of SLE, e.g., evidence of lupus nephritis. Comparative studies between treated and control animals are used to determine the relative efficacy of the test compounds in preventing or ameliorating SLE. A molecule which prevents or ameliorates (decreases or suppresses or relieves or promotes remission of) the symptoms of SLE is considered useful in the invention.

Therapeutic Administration

As demonstrated above, recombinant alpha-fetoprotein, e.g., rHuAFP (or a fragment or analog thereof) is effective in inhibiting proliferation of autoimmune cells and accordingly is useful for the prevention or amelioration of autoimmune diseases including, but not limited to, multiple sclerosis, rheumatoid arthritis, diabetes mellitus, systemic lupus erythematosus, and myasthenia gravis. Accordingly, recombinant human alpha-fetoprotein (or a fragment or analog thereof) can be formulated according to known methods to prepare pharmaceutically useful compositions.

Recombinant alpha-fetoprotein, e.g., rHuAFP (or a fragment or analog thereof), is preferably administered to the patient in an amount which is effective in preventing or ameliorating the symptoms of an autoimmune disease. Generally, a dosage of 0.1 ng/kg to 10 g/kg body is adequate. If desired, administration is performed on a daily basis. Because there are no known adverse side effects related to recombinant human alpha-fetoprotein, it is believed that relatively high dosages can be safely administered. For example, treatment of human patients will be carried out using a therapeutically effective amount of rHuAFP (or a fragment or analog thereof) in a physiologically acceptable carrier. Suitable carriers and their formulation are described for example in Remington's *Pharmaceutical Sciences* by E. W. Martin. The amount of rHuAFP to be administered will vary depending upon the manner of administration, the age and body weight of the patient, and with the type of disease, and size of the patient predisposed to or suffering from the disease. Preferable routes of administration include, for example, subcutaneous, intravenous, intramuscular, or intradermal injections which provide continuous, sustained levels of the drug in the patient. In other preferred routes of administration, rHuAFP can be given to a patient by injection or implantation of a slow release preparation, for example, in a slowly dissociating polymeric or crystalline form; this sort of sustained administration can follow an initial delivery of the drug by more conventional routes (for example, those described above). Alternatively, rHuAFP can be administered using an infusion pump (e.g., an external or implantable infusion pump), thus allowing a precise degree of control over the rate of drug release, or through installation of rHuAFP in the nasal passages in a similar fashion to that used to promote absorption of insulin. As an alternative to nasal transmucosal absorption, rHuAFP can be delivered by aerosol deposition of the powder or solution into the lungs.

Furthermore, the method(s) of the invention can also employ combination therapy in which rHuAFP is administered either simultaneously or sequentially with a therapeutic agent such as a general or specific tolerizing agent (e.g., an anti-idiotypic agent (e.g., a monoclonal) or a therapeutic vaccine or an oral agent (e.g., insulin, collagen or myelin basic protein) or a cytokine (e.g., Il-15) or an interferon (α-interferon) or an immunosuppressive agent. Preferably, an immunosuppressive agent is administered in an effective dose which is lower than the standard dose when the immunosuppressive agent is used by itself. Preferred immunosuppressive agents are cyclosporine, FK-506, steroids, azathioprine, or 15-deoxyspergualin.

Treatment is started generally with the diagnosis or suspicion of an autoimmune disease and is generally repeated on a daily basis. Protection or prevention from the development (or progression or exacerbation) of an autoimmune disease is also achieved by administration of rHuAFP prior to the onset of the disease. If desired, the efficacy of the treatment or protection regimens is assessed with the methods of monitoring or diagnosing patients for autoimmune disease.

The method(s) of the invention can also be used to treat non-human mammals, for example, domestic pets, or livestock.

Other Embodiments

In other embodiments, the invention includes the use of rHuAFP (or fragment or analog thereof) for the prevention or treatment of acquired immunodeficiency syndrome (AIDS). To evaluate the immunosuppressive effect of rHuAFP or a fragment or analog thereof on AIDS, i.e., the compound's ability to prevent or ameliorate an autoimmune component of AIDS, test compounds are administered to an appropriate animal (e.g., a human patient), according to standard methods, e.g., intravenously or intraperitoneally, at an appropriate dosage on a daily basis as is discussed above. Generally, administration is initiated prior to the onset of AIDS and/or after the clinical appearance of AIDS. Control animals receive a placebo, e.g., human serum albumin, similarly administered as for rHuAFP or related molecules. The effect of the test compound on AIDS is monitored according to standard methods. For example, analysis of the ability of the test compound to inhibit or prevent or ameliorate the destruction of helper T cells can be monitored. Comparative studies between treated and control animals are used to determine the relative efficacy of the test compounds in preventing or ameliorating AIDS. A molecule which prevents or ameliorates (decreases or suppresses or relieves or promotes remission of) the symptoms of AIDS is considered useful in the invention.

In the invention also includes the use of a therapeutically effective amount rHuAFP (or fragment or analog thereof) for inhibiting the rejection of a transplanted organ (e.g., the heart, the liver, the lung, the pancreas, and the kidney), tissue (e.g., skin, bone marrow, dura mater, bone, implanted collagen, an implanted bioreactor), or cell (e.g., β islet cells of the pancreas, stem cells, hematopoietic cells, lymph cells, neuroendocrine or adrenal cells) in a mammal. Such transplanted organs, tissues, or cells may be derived from any source, e.g., such biological material can be allogenic, phenogenic, autologous, synthetic, artificial or genetically-engineered. For example, the method can also be used when the patient is the recipient of an allograft such a heart or kidney from another species.

In one working example, the immunosuppressive effect of rHuAFP on clinical transplantation, i.e., the ability of rHuAFP to prevent or ameliorate transplant rejection (e.g., hyperacute rejection, acute rejection and chronic rejection), is evaluated by administering rHuAFP to an NIH minipig according to standard methods, e.g., intravenously or intraperitoneally, at an appropriate dosage on a daily basis. Generally, administration of rHuAFP is initiated prior to the transplant, e.g., transplantation of a kidney and/or after the transplant procedure. Control animals receive a placebo, e.g., human serum albumin, similarly administered as for rHuAFP. The effect of rHuAFP on transplant rejection is monitored according to standard methods. One manifestation of the rejection process is diminished function of the transplanted organ, for example, analysis of urine output can be monitored. If desired, histological inspection (e.g., by using any standard histochemical or immunohistochemical procedure, see e.g., Ausubel et al., supra; Bancroft and Stevens, supra) of kidney tissue is performed and tissue samples obtained by biopsy are examined microscopically for evidence of transplant rejection, e.g., chronic interstitial fibrosis, vascular thrombosis, or the presence of abnormal lymphocytic infiltrates. Comparative studies between treated and control animals are used to determine the relative efficacy of rHuAFP in preventing or ameliorating transplant rejection. Recombinant HuAFP (a fragment or analog thereof) which prevents or ameliorates (decreases or suppresses or relieves or promotes remission of) the symptoms of transplant rejection is considered useful in the invention.

All publications, manufacturer's instructions, patents, and patent applications mentioned in this specification are herein incorporated by reference to the same extent as if each individual publication or patent application was specifically and individually indicated to be incorporated by reference.

What is claimed is:

1. A method of inhibiting autoreactive immune cell proliferation in a mammal, said method comprising administering to said mammal a therapeutically effective amount of recombinant human alpha-fetoprotein or a fragment thereof comprising Domain I, Domain II, Domain III, Domain I+II, Domain II+III, or Fragment I.

2. The method of claim 1, wherein said immune cells include T cells.

3. The method of claim 1, wherein said mammal is a human patient.

4. A method of treating an autoimmune disease in a mammal, said method comprising administering to said mammal a therapeutically effective amount of recombinant human alpha-fetoprotein or a fragment thereof comprising Domain I, Domain II, Domain III, Domain I+II, Domain II+III, or Fragment I.

5. The method of claim 4, wherein said autoimmune disease is multiple sclerosis.

6. The method of claim 4, wherein said autoimmune disease is rheumatoid arthritis.

7. The method of claim 4, wherein said autoimmune disease is myasthenia gravis.

8. The method of claim 4, wherein said autoimmune disease is insulin-dependent diabetes mellitus.

9. The method of claim 4, wherein said autoimmune disease is systemic lupus erythematosus.

10. The method of claim 1, further comprising administering to said mammal an immunosuppressive agent in an effective dose which is lower than the standard dose when said immunosuppressive agent is used by itself.

11. The method of claim 1, further comprising administering to said mammal a tolerizing agent.

12. The method of claim 10, wherein said immunosuppressive agent is cyclosporine.

13. The method of claim 10, wherein said immunosuppresive agent is a steroid, azathioprine, FK-506, or 15-deoxyspergualin.

* * * * *

UNITED STATES PATENT AND TRADEMARK OFFICE
CERTIFICATE OF CORRECTION

PATENT NO. : 6,288,034 B1
DATED : September 11, 2001
INVENTOR(S) : Robert A. Murgita It is certified that error appears in the above-identified patent and that said Letters Patent is hereby corrected as shown below:

Title page,
OTHER PUBLICATIONS, replace the Brenner reference title "Inhibitory Effect Of α-fetoprotein On the Binding Of *Myasthenia gravis* Antibody To Acetylcholine Receptor" with -- Inhibitory Effect Of α-fetoprotein On the Binding Of *Myasthenia gravis* Antibody To Acetylcholine Receptor --;
OTHER PUBLICATIONS, replace the Murgita reference title "Adult murine T cells activated in vitro by α-fetoprotein and naturally occuring T cells in newborn mice: Indentity in function and cell surface differentiation antigens," with -- Adult murine T cells activated in vitro by α-fetoprotein and naturally occurring T cells in newborn mice: Identity in function and cell surface differentiation antigens --;

Column 2,
Line 2, replace "cell e.g.," with -- cell (e.g., --;
Line 29, replace rHuAPP" with -- rHuAFP --;
Line 36, replace "ahd" with -- and --;
Line 47, replace "FIGS. 1A" with -- FIG. 1A --;

Column 3,
Line 5, replace "▲" with -- ▼ --;
Line 11, replace "▲" with -- ▼ --;

Column 6,
Line 56, replace "1X reaction buffer," with -- 10X reaction buffer --;

Column 9,
Lines 6 through 8, put a blank line between "Results are expressed as mean cpm±the standard error of the mean of triplicate or quadruplicate cultures." and "RESULTS";
Line 53, replace "NAb." with -- MAb --;

Column 10,
Line 23, replace "organs-in" with -- organs in --;

Column 12,
Line 29, replace "Torpedo californica" with -- *Torpedo californica* --;
Line 33, replace "(H-2B)" with -- $(H-2^B)$ --;
Line 37, replace "(H-2B)" with -- $(H-2^B)$ --;

UNITED STATES PATENT AND TRADEMARK OFFICE
CERTIFICATE OF CORRECTION

PATENT NO.    : 6,288,034 B1
DATED         : September 11, 2001
INVENTOR(S)   : Robert A. Murgita It is certified that error appears in the above-identified patent and that said Letters Patent is hereby corrected as shown below:

<u>Column 13,</u>
Line 13, replace "*Enal.*" with -- *Engl.* --;
Line 56, replace "control animals" with -- Control animals --;

<u>Column 14,</u>
Line 7, replace "LuPus" with -- Lupus --; and
Line 26, replace "mice-and" with -- mice and --.

Signed and Sealed this

Sixteenth Day of April, 2002

Attest:

JAMES E. ROGAN
Attesting Officer   Director of the United States Patent and Trademark Office